(12) United States Patent
Cuello et al.

(10) Patent No.: US 8,512,702 B2
(45) Date of Patent: Aug. 20, 2013

(54) PROSTATE CANCER DIAGNOSIS AND TREATMENT

(75) Inventors: Claudio Cuello, Westmount (CA); Uri Saragovi, Montreal (CA); Pierre Du Ruisseau, Laval (CA); Phil Gold, Westmount (CA); Nicole Bernard, Greenfield Park (CA); Serge Moffett, Montreal (CA)

(73) Assignee: Proscan Rx Pharma Inc., Montreal (CA)

( * ) Notice: Subject to any disclaimer, the term of this patent is extended or adjusted under 35 U.S.C. 154(b) by 19 days.

(21) Appl. No.: 13/325,126

(22) Filed: Dec. 14, 2011

(65) Prior Publication Data

US 2012/0082618 A1 Apr. 5, 2012

Related U.S. Application Data

(62) Division of application No. 12/879,641, filed on Sep. 10, 2010, now Pat. No. 8,101,713, which is a division of application No. 10/543,572, filed as application No. PCT/CA2004/000127 on Jan. 28, 2004, now Pat. No. 7,811,564.

(60) Provisional application No. 60/442,897, filed on Jan. 28, 2003.

(51) Int. Cl.
*G01N 33/574* (2006.01)

(52) U.S. Cl.
USPC ........ 424/130.1; 530/300; 530/327; 530/350; 530/387.1; 530/387.7; 530/388.22; 530/388.8; 530/391.3; 435/7.23; 424/138.1; 424/148.1; 424/155.1; 424/174.1; 424/178.1

(58) Field of Classification Search
USPC ................... 530/300, 327, 350, 387.1, 387.7, 530/388.22, 388.8, 391.3; 435/7.23; 424/130.1, 138.1, 148.1, 155.1, 174.1, 178.1
See application file for complete search history.

(56) References Cited

U.S. PATENT DOCUMENTS

| | | |
|---|---|---|
| 5,162,504 A | 11/1992 | Horoszewicz |
| 5,763,202 A | 6/1998 | Horoszewicz |
| 6,107,090 A | 8/2000 | Bander |
| 6,150,508 A | 11/2000 | Murphy et al. |

FOREIGN PATENT DOCUMENTS

| | | |
|---|---|---|
| WO | WO-9409820 A1 | 5/1994 |
| WO | WO-9945954 A1 | 9/1999 |
| WO | WO-0050457 A1 | 8/2000 |
| WO | WO-02069907 A2 | 9/2002 |
| WO | WO-02081646 A2 | 10/2002 |
| WO | WO03/034903 | 1/2003 |
| WO | WO-03034903 A2 | 5/2003 |

OTHER PUBLICATIONS

Pirtskhalaishvili G et al Cancer Practice 2001 9(6) :295-306.
Horoszewicz et al. Can Res 1983 43: 1809-1818.
Israeli et al Can Res 1993 53 :227-230.
Horoszewicz et al. Anticancer Res 1987 7 :927-935.
Bander Sem in Oncology 1994 21(5):607-612.
Kohler G and Milstein C Nature 1975 256 (5517):495-497.
Goding J Monoclonal antibodies: principles and practice 1983 pp. 98-118 NY Academic press.
Geysen HM et al. Journal of Immunological methods 1987 Elsevier Science Publishers vol. 102, pp. 259-274.
Houghten RA PNAS 1985 vol. 82 5131-5135.
Holmes EH Expert Opinion on Investigational Drugs 2001 vol. 10, No. 3, pp. 511-519.
Communication on pusruant to Art. 94(3) EPC of EP04705746 dated Apr. 30, 2010.
Communication pusruant to Art. 94(3) EPC of EP04705746 dated Mar. 25, 2008.
Ye (Sheng Wu Gong Cheng Xue Bao). Jan. 2002; 18(1) 35-39) abstract.
Todorova et al., (Cancer Immun. Jan. 11, 2005;5:1; pp. 1-8).
Murphy et al. (J. Urol. Dec. 1998; 160 (6):2396-2401).
Cao et al. (Prostate 2007; 67:1791-1800).
Schmittgen et al. (Int. J. Cancer. 2003; 107:323-329).
Aggarwal et al. (Prostate. 2006; 66: 903-910).
Smith-Jones PM et al. (Cancer Res. 2000; 60(18):5237-5243).
Moffett S. et al., (Hybridoma, 2007; 26(6): 363-372).

*Primary Examiner* — Stephen Rawlings

(74) *Attorney, Agent, or Firm* — Fasken Martineau Dumoulin, LLP

(57) ABSTRACT

The present invention relates to novel antibodies and their use for detecting, imaging, staging, treating and monitoring of prostate cancer, and/or metastasis thereof. The present invention also relates to novel pharmaceutical compositions for the treatment of prostate cancer. Furthermore the present invention relates to assay systems and kits for detecting, imaging, staging, treating and monitoring of prostate cancer, and/or metastasis thereof.

6 Claims, 10 Drawing Sheets

```
ATGTGGAATCTCCTTCACGAAACCGACTCGGCTGTGGCCACCGCGCGCCGCCCGC
GCTGGCTGTGCGCTGGGGCGCTGGTGCTGGCGGGTGGCTTCTTTCTCCTCGGCTTC
CTCTTCGGGTGGTTTATAAAATCCTCCAATGAAGCTACTAACATTACTCCAAAGC
ATAATATGAAAGCATTTTTGGATGAATTGAAAGCTGAGAACATCAAGAAGTTCTT
ATATAATTTTACACAGATACCACATTTAGCAGGAACAGAACAAAACTTTCAGCTT
GCAAAGCAAATTCAATCCCAGTGGAAAGAATTTGGCCTGGATTCTGTTGAGCTAG
CACATTATGATGTCCTGTTGTCCTACCCAAATAAGACTCATCCCAACTACATCTCA
ATAATTAATGAAGATGGAAATGAGATTTTCAACACATCATTATTTGAACCACCTC
CTCCAGGATATGAAAATGTTTCGGATATTGTACCACCTTTCAGTGCTTTCTCTCCT
CAAGGAATGCCAGAGGGCGATCTAGTGTATGTTAACTATGCACGAACTGAAGAC
TTCTTTAAATTGGAACGGGACATGAAAATCAATTGCTCTGGGAAAATTGTAATTG
CCAGATATGGGAAAGTTTTCAGAGGAAATAAGGTTAAAAATGCCCAGCTGGCAG
GGGCCAAAGGAGTCATTCTCTACTCCGACCCTGCTGACTACTTTGCTCCTGGGGT
GAAGTCCTATCCAGATGGTTGGAATCTTCCTGGAGGTGGTGTCCAGCGTGGAAAT
ATCCTAAATCTGAATGGTGCAGGAGACCCTCTCACACCAGGTTACCCAGCAAATG
AATATGCTTATAGGCGTGGAATTGCAGAGGCTGTTGGTCTTCCAAGTATTCCTGTT
CATCCAATTGGATACTATGATGCACAGAAGCTCCTAGAAAAAATGGGTGGCTCAG
CACCACCAGATAGCAGCTGGAGAGGAAGTCTCAAAGTGCCCTACAATGTTGGAC
CTGGCTTTACTGGAAACTTTTCTACACAAAAAGTCAAGATGCACATCCACTCTAC
CAATGAAGTGACAAGAATTTACAATGTGATAGGTACTCTCAGAGGAGCAGTGGA
ACCAGACAGATATGTCATTCTGGGAGGTCACCGGGACTCATGGGTGTTTGGTGGT
ATTGACCCTCAGAGTGGAGCAGCTGTTGTTCATGAAATTGTGAGGAGCTTTGGAA
CACTGAAAAAGGAAGGGTGGAGACCTAGAAGAACAATTTTGTTTGCAAGCTGGG
ATGCAGAAGAATTTGGTCTTCTTGGTTCTACTGAGTGGGCAGAGGAGAATTCAAG
ACTCCTTCAAGAGCGTGGCGTGGCTTATATTAATGCTGACTCATCTATAGAAGGA
AACTACACTCTGAGAGTTGATTGTACACCGCTGATGTACAGCTTGGTACACAACC
TAACAAAAGAGCTGAAAAGCCCTGATGAAGGCTTTGAAGGCAAATCTCTTTATGA
AAGTTGGACTAAAAAAAGTCCTTCCCCAGAGTTCAGTGGCATGCCCAGGATAAGC
AAATTGGGATCTGGAAATGATTTGAGGTGTTCTTCCAACGACTTGGAATTGCTTC
AGGCAGAGCACGGTATACTAAAAATTGGGAAACAAACAAATTCAGCGGCTATCC
ACTGTATCACAGTGTCTATGAAACATATGAGTTGGTGGAAAAGTTTTATGATCCA
ATGTTTAAATATCACCTCACTGTGGCCCAGGTTCGAGGAGGGATGGTGTTTGAGC
TAGCCAATTCCATAGTGCTCCCTTTTGATTGTCGAGATTATGCTGTAGTTTTAAGA
AAGTATGCTGACAAAATCTACAGTATTTCTATGAAACATCCACAGGAAATGAAGA
CATACAGTGTATCATTTGATTCACTTTTTTCTGCAGTAAAGAATTTTACAGAAATT
GCTTCCAAGTTCAGTGAGAGACTCCAGGACTTTGACAAAGCAACCCAATAGTAT
TAAGAATGATGAATGATCAACTCATGTTTCTGGAAAGAGCATTTATTGATCCATT
AGGGTTACCAGACAGGCCTTTTTATAGGCATGTCATCTATGCTCCAAGCAGCCAC
AACAAGTATGCAGGGGAGTCATTCCCAGGAATTTATGATGCTCTGTTTGATATTG
AAAGCAAAGTGGACCCTTCCAAGGCCTGGGGAGAAGTGAAGAGACAGATTTATG
TTGCAGCCTTCACAGTGCAGGCAGCTGCAGAGACTTTGAGTGAAGTAGCCTAA
```

FIG. 1

MWNLLHETDSAVATARRPRWLCAGALVLAGGFFLLGFLFGWFIKSSNEATNITPKHN
MKAFLDELKAENIKKFLYNFTQIPHLAGTEQNFQLAKQIQSQWKEFGLDSVELAHYD
VLLSYPNKTHPNYISIINEDGNEIFNTSLFEPPPPGYENVSDIVPPFSAFSPQGMPEGDLV
YVNYARTEDFFKLERDMKINCSGKIVIARYGKVFRGNKVKNAQLAGAKGVILYSDP
ADYFAPGVKSYPDGWNLPGGGVQRGNILNLNGAGDPLTPGYPANEYAYRRGIAEAV
GLPSIPVHPIGYYDAQKLLEKMGGSAPPDSSWRGSLKVPYNVGPGFTGNFSTQKVKM
HIHSTNEVTRIYNVIGTLRGAVEPDRYVILGGHRDSWVFGGIDPQSGAAVVHEIVRSF
GTLKKEGWRPRRTILFASWDAEEFGLLGSTEWAEENSRLLQERGVAYINADSSIEGN
YTLRVDCTPLMYSLVHNLTKELKSPDEGFEGKSLYESWTKKSPSPEFSGMPRISKLGS
GNDFEVFFQRLGIASGRARYTKNWETNKFSGYPLYHSVYETYELVEKFYDPMFKYH
LTVAQVRGGMVFELANSIVLPFDCRDYAVVLRKYADKIYSISMKHPQEMKTYSVSFD
SLFSAVKNFTEIASKFSERLQDFDKSNPIVLRMMNDQLMFLERAFIDPLGLPDRPFYRH
VIYAPSSHNKYAGESFPGIYDALFDIESKVDPSKAWGEVKRQIYVAAFTVQAAAETLS
EVA

FIG. 2

FIG_4

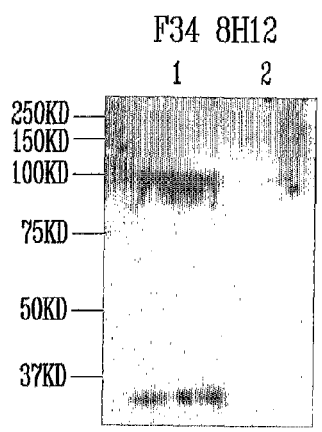 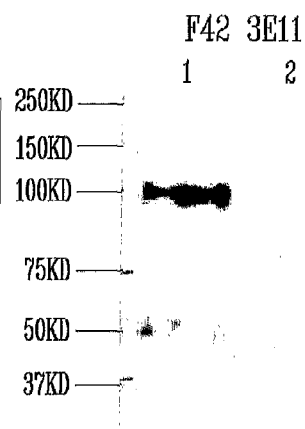 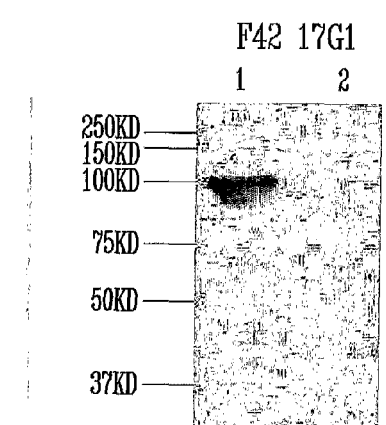 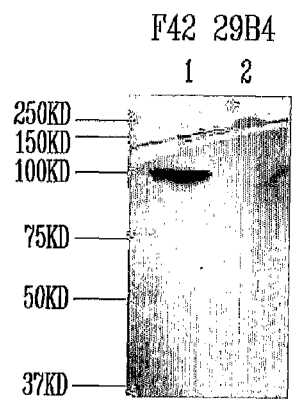 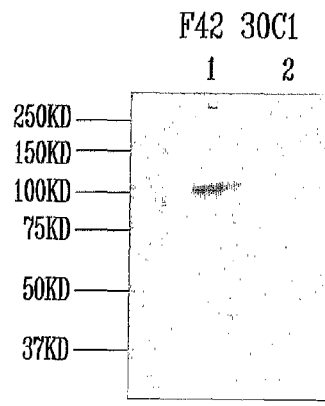 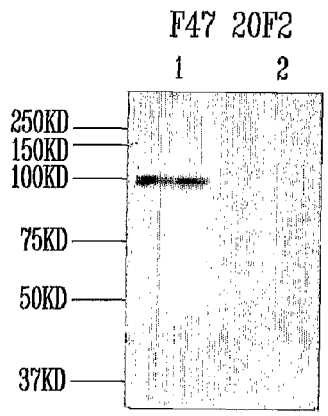
FIG. 5

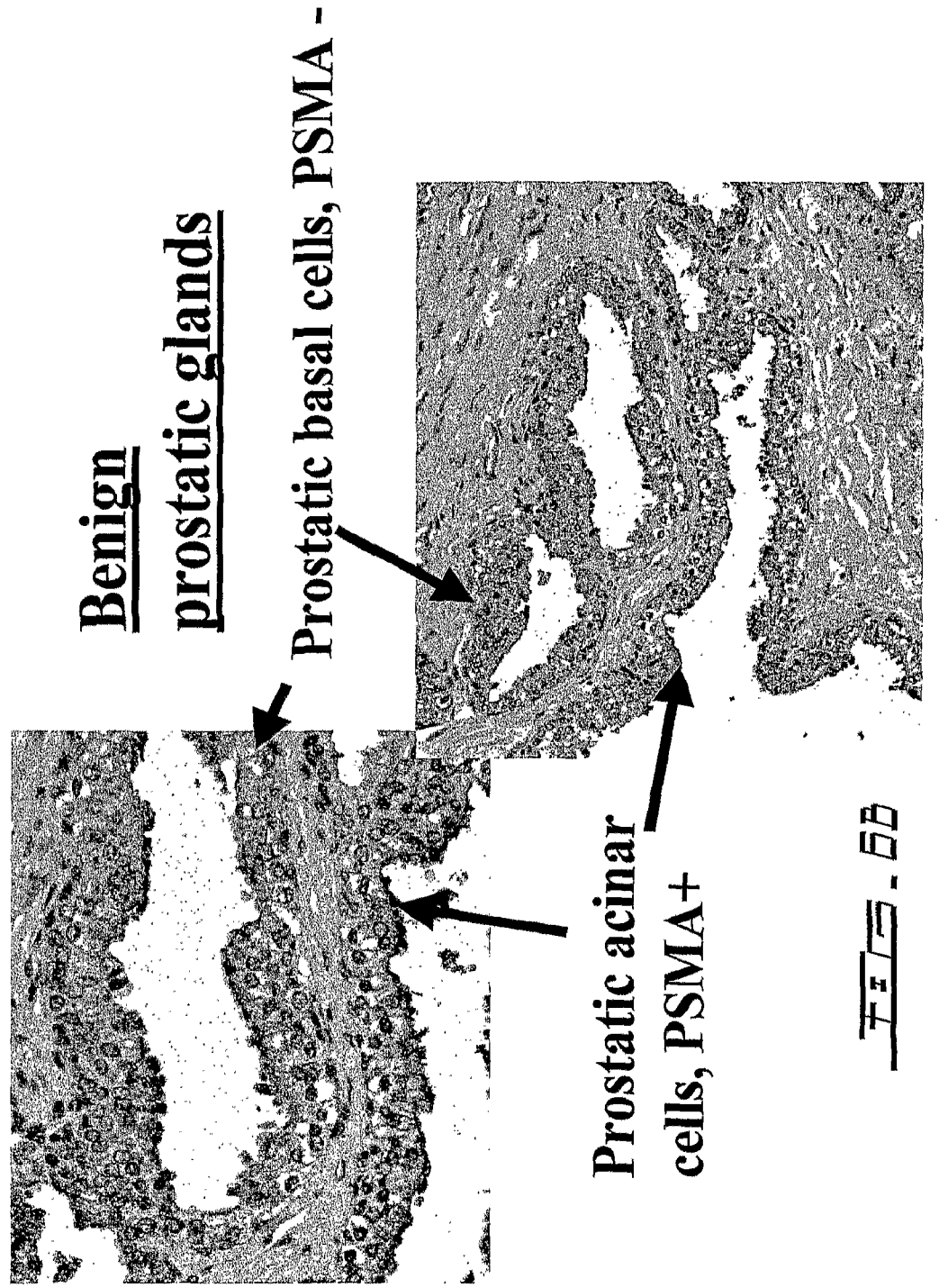

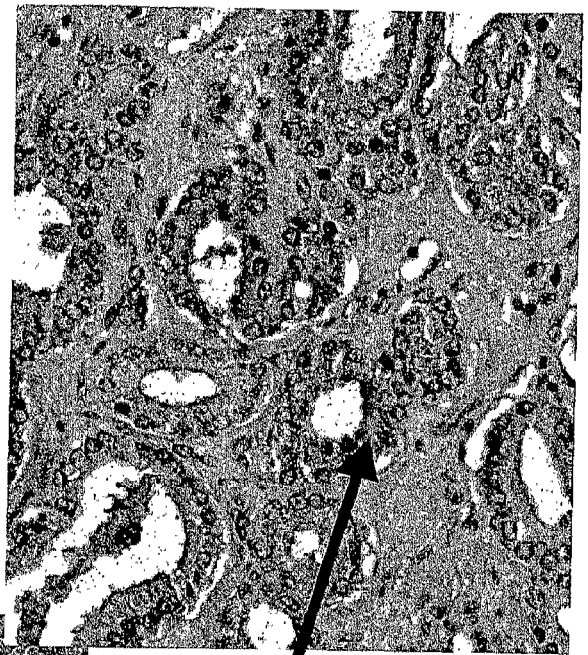
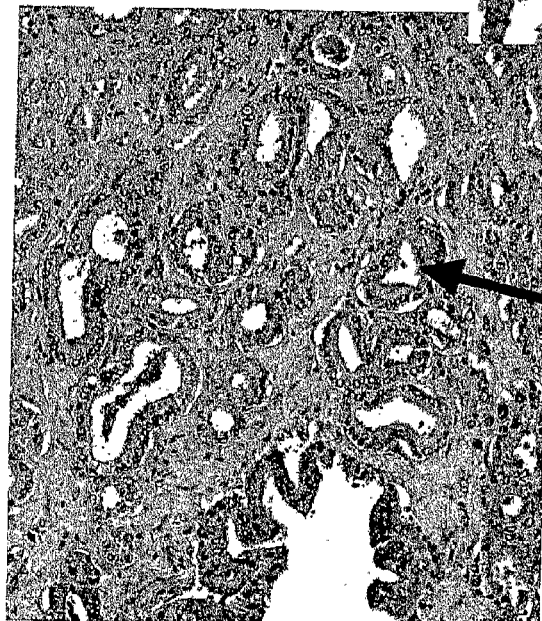
Prostate cancer
Prostate cancer, Gleason 3+3=6, PSMA+
FIG. 6C

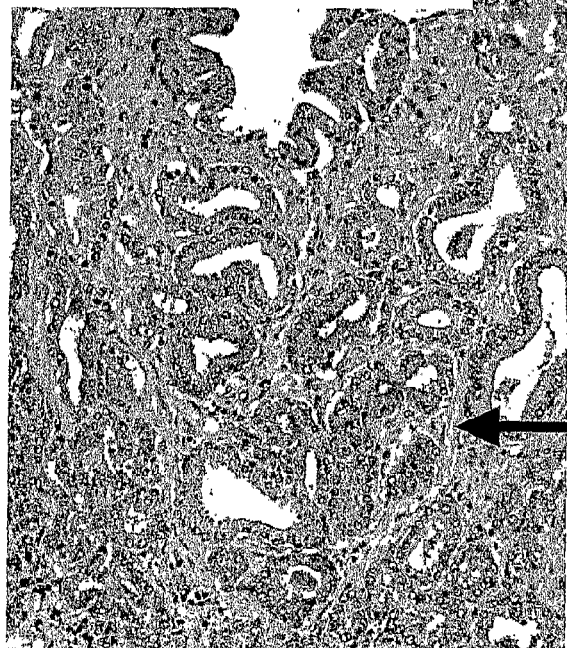
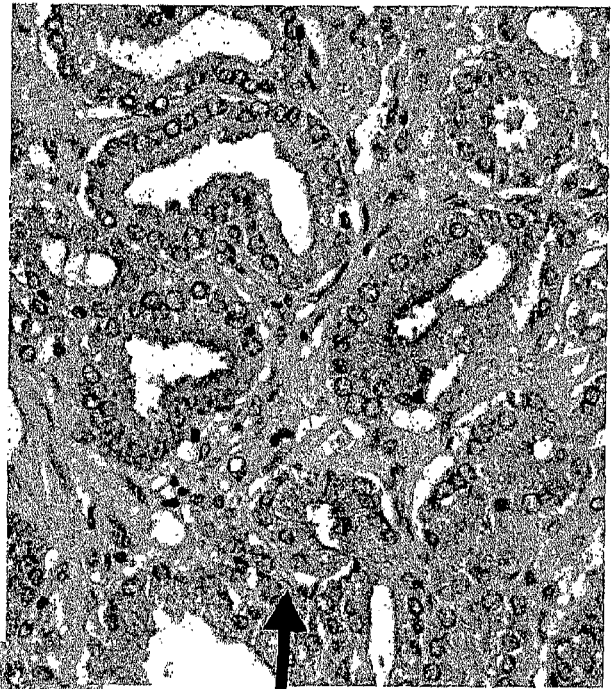
FIG. 60
Prostate cancer
Prostate cancer, Gleason 3+3=6, PSMA +

SEQUENCE LISTING

```
<160> NUMBER OF SEQ ID NOS: 36

<210> SEQ ID NO 1
<211> LENGTH: 18
<212> TYPE: PRT
<213> ORGANISM: Artificial Sequence
<220> FEATURE:
<223> OTHER INFORMATION: Chemically synthesized peptide

<400> SEQUENCE: 1

Cys Asn Ile Thr Pro Lys His Asn Met Lys Ala Phe Leu Asp Glu Leu
1               5                   10                  15

Lys Ala

<210> SEQ ID NO 2
<211> LENGTH: 19
<212> TYPE: PRT
<213> ORGANISM: Artificial Sequence
<220> FEATURE:
<223> OTHER INFORMATION: Chemically synthesized peptide

<400> SEQUENCE: 2

Cys Gly Thr Glu Gln Asn Phe Gln Leu Ala Lys Gln Ile Gln Ser Gln
1               5                   10                  15

Trp Lys Glu

<210> SEQ ID NO 3
<211> LENGTH: 16
<212> TYPE: PRT
<213> ORGANISM: Artificial Sequence
<220> FEATURE:
<223> OTHER INFORMATION: Chemically synthesized peptide
```

```
<400> SEQUENCE: 3

Cys Gly Leu Asp Ser Val Glu Leu Ala His Tyr Asp Val Leu Leu Ser
1               5                   10                  15

<210> SEQ ID NO 4
<211> LENGTH: 14
<212> TYPE: PRT
<213> ORGANISM: Artificial Sequence
<220> FEATURE:
<223> OTHER INFORMATION: Chemically synthesized peptide

<400> SEQUENCE: 4

Cys Phe Ser Ala Phe Ser Pro Gln Gly Met Pro Glu Gly Asp
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Chemically synthesized peptide

<400> SEQUENCE: 5

Cys Ala Pro Gly Val Lys Ser Tyr Pro Asp Gly
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Chemically synthesized peptide

<400> SEQUENCE: 6

Cys Ala Tyr Arg Arg Gly Ile Ala Glu Ala Val Gly
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Chemically synthesized peptide

<400> SEQUENCE: 7

Cys His Ile His Ser Thr Asn Glu Val Thr Arg
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Chemically synthesized peptide

<400> SEQUENCE: 8

Cys Gly Lys Ser Leu Tyr Glu Ser Trp Thr Lys Lys
1               5                   10

<210> SEQ ID NO 9
<211> LENGTH: 16
<212> TYPE: PRT
<213> ORGANISM: Artificial Sequence
<220> FEATURE:
<223> OTHER INFORMATION: Chemically synthesized peptide

<400> SEQUENCE: 9
```

```
Cys Ala Ser Gly Arg Ala Arg Tyr Thr Lys Asn Trp Glu Thr Asn Lys
1               5                   10                  15

<210> SEQ ID NO 10
<211> LENGTH: 18
<212> TYPE: PRT
<213> ORGANISM: Artificial Sequence
<220> FEATURE:
<223> OTHER INFORMATION: Chemically synthesized peptide

<400> SEQUENCE: 10

Cys Leu Tyr His Ser Val Tyr Glu Thr Tyr Glu Leu Val Glu Lys Phe
1               5                   10                  15

Tyr Asp

<210> SEQ ID NO 11
<211> LENGTH: 13
<212> TYPE: PRT
<213> ORGANISM: Artificial Sequence
<220> FEATURE:
<223> OTHER INFORMATION: Chemically synthesized peptide

<400> SEQUENCE: 11

Cys Ala Asp Lys Ile Tyr Ser Ile Ser Met Lys His Pro
1               5                   10

<210> SEQ ID NO 12
<211> LENGTH: 19
<212> TYPE: PRT
<213> ORGANISM: Artificial Sequence
<220> FEATURE:
<223> OTHER INFORMATION: Chemically synthesized peptide

<400> SEQUENCE: 12

Cys Cys Ser Glu Arg Leu Gln Asp Phe Asp Lys Ser Asn Pro Ile Val
1               5                   10                  15

Leu Arg Cys

<210> SEQ ID NO 13
<211> LENGTH: 10
<212> TYPE: PRT
<213> ORGANISM: Artificial Sequence
<220> FEATURE:
<223> OTHER INFORMATION: Chemically synthesized peptide

<400> SEQUENCE: 13

Cys Glu Ser Lys Val Asp Pro Ser Lys Ala
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Chemically synthesized peptide

<400> SEQUENCE: 14

Cys Thr Val Gln Ala Ala Ala Glu Thr Leu Ser Glu Val Ala
1               5                   10

<210> SEQ ID NO 15
<211> LENGTH: 24
<212> TYPE: DNA
<213> ORGANISM: Artificial Sequence
<220> FEATURE:
<223> OTHER INFORMATION: primer
```

-continued

```
<400> SEQUENCE: 15
atgtggaatc tccttcacga aacc                                          24

<210> SEQ ID NO 16
<211> LENGTH: 24
<212> TYPE: DNA
<213> ORGANISM: Artificial Sequence
<220> FEATURE:
<223> OTHER INFORMATION: primer

<400> SEQUENCE: 16
ttaggctact tcactcaaag tctc                                          24

<210> SEQ ID NO 17
<211> LENGTH: 27
<212> TYPE: DNA
<213> ORGANISM: Artificial Sequence
<220> FEATURE:
<223> OTHER INFORMATION: primer

<400> SEQUENCE: 17
ggggatccat gtggaatctc cttcacg                                       27

<210> SEQ ID NO 18
<211> LENGTH: 29
<212> TYPE: DNA
<213> ORGANISM: Artificial Sequence
<220> FEATURE:
<223> OTHER INFORMATION: primer

<400> SEQUENCE: 18
gggctcgagg gctacttcac tcaaagtct                                     29

<210> SEQ ID NO 19
<211> LENGTH: 33
<212> TYPE: DNA
<213> ORGANISM: Artificial Sequence
<220> FEATURE:
<223> OTHER INFORMATION: primer

<400> SEQUENCE: 19
ggggatccga aatcctccaa tgaagctact aac                                33

<210> SEQ ID NO 20
<211> LENGTH: 33
<212> TYPE: DNA
<213> ORGANISM: Artificial Sequence
<220> FEATURE:
<223> OTHER INFORMATION: primer

<400> SEQUENCE: 20
gggctcgagt taggctactt cactcaaagt ctc                                33

<210> SEQ ID NO 21
<211> LENGTH: 2253
<212> TYPE: DNA
<213> ORGANISM: Homo sapiens

<400> SEQUENCE: 21
atgtggaatc tccttcacga aaccgactcg gctgtggcca ccgcgcgccg cccgcgctgg    60
ctgtgcgctg gggcgctggt gctggcgggt ggcttctttc tcctcggctt cctcttcggg   120
tggtttataa atcctccaa tgaagctact aacattactc caaagcataa tatgaaagca   180
tttttggatg aattgaaagc tgagaacatc aagaagttct tatataattt tacacagata   240
```

```
ccacatttag caggaacaga acaaaacttt cagcttgcaa agcaaattca atcccagtgg      300
aaagaatttg gcctggattc tgttgagcta gcacattatg atgtcctgtt gtcctaccca      360
aataagactc atcccaacta catctcaata attaatgaag atggaaatga gattttcaac      420
acatcattat ttgaaccacc tcctccagga tatgaaaatg tttcggatat tgtaccacct      480
ttcagtgctt tctctcctca aggaatgcca gagggcgatc tagtgtatgt taactatgca      540
cgaactgaag acttctttaa attggaacgg gacatgaaaa tcaattgctc tgggaaaatt      600
gtaattgcca gatatgggaa agttttcaga ggaaataagg ttaaaaatgc ccagctggca      660
ggggccaaag gagtcattct ctactccgac cctgctgact actttgctcc tggggtgaag      720
tcctatccag atggttggaa tcttcctgga ggtggtgtcc agcgtggaaa tatcctaaat      780
ctgaatggtg caggagaccc tctcacacca ggttacccag caaatgaata tgcttatagg      840
cgtggaattg cagaggctgt tggtcttcca agtattcctg ttcatccaat tggatactat      900
gatgcacaga agctcctaga aaaaatgggt ggctcagcac caccagatag cagctggaga      960
ggaagtctca aagtgcccta caatgttgga cctggcttta ctggaaactt ttctacacaa     1020
aaagtcaaga tgcacatcca ctctaccaat gaagtgacaa gaatttacaa tgtgataggt     1080
actctcagag gagcagtgga accagacaga tatgtcattc tgggaggtca ccgggactca     1140
tgggtgtttg gtggtattga ccctcagagt ggagcagctg ttgttcatga aattgtgagg     1200
agctttggaa cactgaaaaa ggaagggtgg agacctagaa gaacaatttt gtttgcaagc     1260
tgggatgcag aagaatttgg tcttcttggt tctactgagt gggcagagga gaattcaaga     1320
ctccttcaag agcgtggcgt ggcttatatt aatgctgact catctataga aggaaactac     1380
actctgagag ttgattgtac accgctgatg tacagcttgg tacacaacct aacaaaagag     1440
ctgaaaagcc ctgatgaagg ctttgaaggc aaatctcttt atgaaagttg gactaaaaaa     1500
agtccttccc cagagttcag tggcatgccc aggataagca aattgggatc tggaaatgat     1560
tttgaggtgt tcttccaacg acttggaatt gcttcaggca gcacggta tactaaaaat      1620
tgggaaacaa acaaattcag cggctatcca ctgtatcaca gtgtctatga acatatgag      1680
ttggtggaaa agttttatga tccaatgttt aaatatcacc tcactgtggc ccaggttcga     1740
ggagggatgg tgtttgagct agccaattcc atagtgctcc ctttgattg tcgagattat     1800
gctgtagttt taagaaagta tgctgacaaa atctacagta tttctatgaa acatccacag     1860
gaaatgaaga catacagtgt atcatttgat tcacttttt ctgcagtaaa gaattttaca     1920
gaaattgctt ccaagttcag tgagagactc caggactttg acaaaagcaa cccaatagta     1980
ttaagaatga tgaatgatca actcatgttt ctggaaagag catttattga tccattaggg     2040
ttaccagaca ggccttttta taggcatgtc atctatgctc caagcagcca acaagtat      2100
gcagggagt cattcccagg aatttatgat gctctgtttg atattgaaag caaagtggac     2160
ccttccaagg cctggggaga agtgaagaga cagatttatg ttgcagcctt cacagtgcag     2220
gcagctgcag agactttgag tgaagtagcc taa                                  2253
```

<210> SEQ ID NO 22
<211> LENGTH: 750
<212> TYPE: PRT
<213> ORGANISM: Homo sapiens

<400> SEQUENCE: 22

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe

-continued

```
                20                  25                  30
Phe Leu Leu Gly Phe Leu Phe Gly Trp Phe Ile Lys Ser Ser Asn Glu
             35                  40                  45
Ala Thr Asn Ile Thr Pro Lys His Asn Met Lys Ala Phe Leu Asp Glu
 50                  55                  60
Leu Lys Ala Glu Asn Ile Lys Lys Phe Leu Tyr Asn Phe Thr Gln Ile
 65                  70                  75                  80
Pro His Leu Ala Gly Thr Glu Gln Asn Phe Gln Leu Ala Lys Gln Ile
                 85                  90                  95
Gln Ser Gln Trp Lys Glu Phe Gly Leu Asp Ser Val Glu Leu Ala His
            100                 105                 110
Tyr Asp Val Leu Leu Ser Tyr Pro Asn Lys Thr His Pro Asn Tyr Ile
            115                 120                 125
Ser Ile Ile Asn Glu Asp Gly Asn Glu Ile Phe Asn Thr Ser Leu Phe
130                 135                 140
Glu Pro Pro Pro Gly Tyr Glu Asn Val Ser Asp Ile Val Pro Pro
145                 150                 155                 160
Phe Ser Ala Phe Ser Pro Gln Gly Met Pro Glu Gly Asp Leu Val Tyr
                165                 170                 175
Val Asn Tyr Ala Arg Thr Glu Asp Phe Phe Lys Leu Glu Arg Asp Met
            180                 185                 190
Lys Ile Asn Cys Ser Gly Lys Ile Val Ile Ala Arg Tyr Gly Lys Val
            195                 200                 205
Phe Arg Gly Asn Lys Val Lys Asn Ala Gln Leu Ala Gly Ala Lys Gly
            210                 215                 220
Val Ile Leu Tyr Ser Asp Pro Ala Asp Tyr Phe Ala Pro Gly Val Lys
225                 230                 235                 240
Ser Tyr Pro Asp Gly Trp Asn Leu Pro Gly Gly Val Gln Arg Gly
                245                 250                 255
Asn Ile Leu Asn Leu Asn Gly Ala Gly Asp Pro Leu Thr Pro Gly Tyr
            260                 265                 270
Pro Ala Asn Glu Tyr Ala Tyr Arg Arg Gly Ile Ala Glu Ala Val Gly
            275                 280                 285
Leu Pro Ser Ile Pro Val His Pro Ile Gly Tyr Tyr Asp Ala Gln Lys
            290                 295                 300
Leu Leu Glu Lys Met Gly Gly Ser Ala Pro Pro Asp Ser Ser Trp Arg
305                 310                 315                 320
Gly Ser Leu Lys Val Pro Tyr Asn Val Gly Pro Gly Phe Thr Gly Asn
            325                 330                 335
Phe Ser Thr Gln Lys Val Lys Met His Ile His Ser Thr Asn Glu Val
            340                 345                 350
Thr Arg Ile Tyr Asn Val Ile Gly Thr Leu Arg Gly Ala Val Glu Pro
            355                 360                 365
Asp Arg Tyr Val Ile Leu Gly Gly His Arg Asp Ser Trp Val Phe Gly
            370                 375                 380
Gly Ile Asp Pro Gln Ser Gly Ala Ala Val His Glu Ile Val Arg
385                 390                 395                 400
Ser Phe Gly Thr Leu Lys Lys Glu Gly Trp Arg Pro Arg Arg Thr Ile
                405                 410                 415
Leu Phe Ala Ser Trp Asp Ala Glu Glu Phe Gly Leu Leu Gly Ser Thr
            420                 425                 430
Glu Trp Ala Glu Glu Asn Ser Arg Leu Leu Gln Glu Arg Gly Val Ala
            435                 440                 445
```

-continued

```
Tyr Ile Asn Ala Asp Ser Ser Ile Glu Gly Asn Tyr Thr Leu Arg Val
            450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                    485                 490                 495

Trp Thr Lys Lys Ser Pro Ser Pro Glu Phe Ser Gly Met Pro Arg Ile
                500                 505                 510

Ser Lys Leu Gly Ser Gly Asn Asp Phe Glu Val Phe Phe Gln Arg Leu
            515                 520                 525

Gly Ile Ala Ser Gly Arg Ala Arg Tyr Thr Lys Asn Trp Glu Thr Asn
530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
                580                 585                 590

Leu Pro Phe Asp Cys Arg Asp Tyr Ala Val Val Leu Arg Lys Tyr Ala
            595                 600                 605

Asp Lys Ile Tyr Ser Ile Ser Met Lys His Pro Gln Glu Met Lys Thr
610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
                660                 665                 670

Arg Ala Phe Ile Asp Pro Leu Gly Leu Pro Asp Arg Pro Phe Tyr Arg
            675                 680                 685

His Val Ile Tyr Ala Pro Ser Ser His Asn Lys Tyr Ala Gly Glu Ser
690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
                740                 745                 750
```

<210> SEQ ID NO 23
<211> LENGTH: 17
<212> TYPE: PRT
<213> ORGANISM: Artificial Sequence
<220> FEATURE:
<223> OTHER INFORMATION: Chemically synthesized peptide

<400> SEQUENCE: 23

```
Asn Ile Thr Pro Lys His Asn Met Lys Ala Phe Leu Asp Glu Leu Lys
1               5                   10                  15

Ala
```

<210> SEQ ID NO 24
<211> LENGTH: 18
<212> TYPE: PRT
<213> ORGANISM: Artificial Sequence
<220> FEATURE:
<223> OTHER INFORMATION: Chemically synthesized peptide

```
<400> SEQUENCE: 24

Gly Thr Glu Gln Asn Phe Gln Leu Ala Lys Gln Ile Gln Ser Gln Trp
1               5                   10                  15

Lys Glu

<210> SEQ ID NO 25
<211> LENGTH: 15
<212> TYPE: PRT
<213> ORGANISM: Artificial Sequence
<220> FEATURE:
<223> OTHER INFORMATION: Chemically synthesized peptide

<400> SEQUENCE: 25

Gly Leu Asp Ser Val Glu Leu Ala His Tyr Asp Val Leu Leu Ser
1               5                   10                  15

<210> SEQ ID NO 26
<211> LENGTH: 13
<212> TYPE: PRT
<213> ORGANISM: Artificial Sequence
<220> FEATURE:
<223> OTHER INFORMATION: Chemically synthesized peptide

<400> SEQUENCE: 26

Phe Ser Ala Phe Ser Pro Gln Gly Met Pro Glu Gly Asp
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Chemically synthesized peptide

<400> SEQUENCE: 27

Ala Pro Gly Val Lys Ser Tyr Pro Asp Gly
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Chemically synthesized peptide

<400> SEQUENCE: 28

Ala Tyr Arg Arg Gly Ile Ala Glu Ala Val Gly
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Chemically synthesized peptide

<400> SEQUENCE: 29

His Ile His Ser Thr Asn Glu Val Thr Arg
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Chemically synthesized peptide
```

```
<400> SEQUENCE: 30

Gly Lys Ser Leu Tyr Glu Ser Trp Thr Lys Lys
1               5                   10

<210> SEQ ID NO 31
<211> LENGTH: 15
<212> TYPE: PRT
<213> ORGANISM: Artificial Sequence
<220> FEATURE:
<223> OTHER INFORMATION: Chemically synthesized peptide

<400> SEQUENCE: 31

Ala Ser Gly Arg Ala Arg Tyr Thr Lys Asn Trp Glu Thr Asn Lys
1               5                   10                  15

<210> SEQ ID NO 32
<211> LENGTH: 17
<212> TYPE: PRT
<213> ORGANISM: Artificial Sequence
<220> FEATURE:
<223> OTHER INFORMATION: Chemically synthesized peptide

<400> SEQUENCE: 32

Leu Tyr His Ser Val Tyr Glu Thr Tyr Glu Leu Val Glu Lys Phe Tyr
1               5                   10                  15

Asp

<210> SEQ ID NO 33
<211> LENGTH: 12
<212> TYPE: PRT
<213> ORGANISM: Artificial Sequence
<220> FEATURE:
<223> OTHER INFORMATION: Chemically synthesized peptide

<400> SEQUENCE: 33

Ala Asp Lys Ile Tyr Ser Ile Ser Met Lys His Pro
1               5                   10

<210> SEQ ID NO 34
<211> LENGTH: 18
<212> TYPE: PRT
<213> ORGANISM: Artificial Sequence
<220> FEATURE:
<223> OTHER INFORMATION: Chemically synthesized peptide

<400> SEQUENCE: 34

Cys Ser Glu Arg Leu Gln Asp Phe Asp Lys Ser Asn Pro Ile Val Leu
1               5                   10                  15

Arg Cys

<210> SEQ ID NO 35
<211> LENGTH: 9
<212> TYPE: PRT
<213> ORGANISM: Artificial Sequence
<220> FEATURE:
<223> OTHER INFORMATION: Chemically synthesized peptide

<400> SEQUENCE: 35

Glu Ser Lys Val Asp Pro Ser Lys Ala
1               5
```

```
<210> SEQ ID NO 36
<211> LENGTH: 13
<212> TYPE: PRT
<213> ORGANISM: Artificial Sequence
<220> FEATURE:
<223> OTHER INFORMATION: Chemically synthesized peptide

<400> SEQUENCE: 36

Thr Val Gln Ala Ala Ala Glu Thr Leu Ser Glu Val Ala
1               5                   10
```

PROSTATE CANCER DIAGNOSIS AND TREATMENT

CROSS-REFERENCE TO RELATED APPLICATIONS

The present application is a divisional application of U.S. patent application Ser. No. 12/879,641, filed on Mar. 17, 2011, now U.S. Pat. No. 8,101,713, which is a divisional application of U.S. patent application Ser. No. 10/543,572, filed on Jan. 28, 2004, now U.S. Pat. No. 7,811,564 issued on Oct. 12, 2010, which is a national phase application of international application serial No. PCT/CA2004/000127, filed Jan. 28, 2004, which claims priority to U.S. Provisional patent application Ser. No. 60/442,897, filed Jan. 28, 2003, the entire disclosures of all of which are incorporated herein by reference.

BACKGROUND OF THE INVENTION (a) Field of the Invention

The invention relates to novel antibodies and their use for detecting, imaging, staging, treating and monitoring of prostate cancer, and/or metastasis thereof. Furthermore, the invention also relates to novel pharmaceutical compositions for the treatment of prostate cancer.

(b) Description of Prior Art

The prostate gland is affected by various significant pathological conditions as benign growth (BPH), infection (prostatitis), and neoplasia (prostate cancer).

Prostate cancer is the second most frequently diagnosed cancer in Canadian and American men, after non-melanoma skin cancer, which is rarely fatal. More importantly, after lung cancer, prostate cancer is the most common cause of cancer-related death. The risk of developing prostate cancer increases significantly with age, particularly for men over 50. For men under 50 years of age the disease is uncommon and death from it is rare.

Prostate cancer accounts for an estimated 28% of newly diagnosed cancer in Canadian men and more than 12% of cancer-related deaths. The current lifetime risk of a Canadian man being diagnosed with prostate cancer is about 1 in 8. In the United States, prostate cancer accounts for approximately 32% of male cancer diagnoses and 14% of cancer deaths. Studies in the United States suggest that the incidence rate may be approaching 1 in 6 men.

Because the incidence of prostate cancer increases with age, it is clear that the burden of this illness will increase dramatically in the coming decades. The aging of the population, particularly the baby boomers, will have important long-term implications for the number of new cases diagnosed. Demographic trends in the next two decades will increase the population at risk for prostate cancer. Statistics Canada projections indicate that the population of men over age 50 will increase from 3.9 million in 1999 to 5.6 million in 2011 (44% increase) and 6.3 million in 2016 (62% increase). The United States Census Bureau projections indicate that the population of men over age 50 will increase from 33.8 million in 1999 to 45.8 million in 2011 (36% increase) and 50.7 million in 2016 (50% increase). The American Cancer Society predicts that there will be about 180,400 new cases of prostate cancer in the United States in the year 2000, and about 31,900 American men will die of the disease.

As a consequence of the expected increases in the number of cases of prostate cancer in the coming years due to rising incidence rates and the aging North American population, more resources will likely be allocated to screening men over 50 for this condition, therefore yielding an increase in the number of cases of identified prostate cancer.

Prostate cancer often exhibits a long latency period. However, it is believed that prostate cancer often remains undetected. Also, because it possesses a high metastatic potential to bone and the lymph nodes, with <10% of individuals diagnosed with prostate cancer also demonstrated, by radionuclide scans, to have bone metastasis, prompt detection and treatment is needed to limit mortality caused by this disease. A recent review of treatment of prostate cancer is by Pirtskhalaishvilig et al. (2001, Cancer Practice 9(6):295).

Increased detection of prostate cancer is due in part to increased awareness and the widespread use of clinical markers such as prostate specific antigen (PSA). Prostate specific antigen is a protein that is produced in very high concentrations in prostate cancer cells. Cancer development results in an altered and subsequent loss of normal gland architecture. This in turn leads to an inability to remove secretions and thus the secretions reach the serum. Serum PSA measurement is one method for screening for prostate cancer.

The current diagnostic and treatment paradigm for prostate cancer is reflected in Clinical Practice Guidelines that are widely available to practicing physicians. The guidelines presented below outline the common approach to the detection and management of prostate cancer.

The Prostate Specific Antigen test is a blood test used to detect prostate cancer in the earliest stages and should be offered annually to men 50 and older with a life expectancy of 10 years or more, and to younger men at high risk for prostate cancer.

The Digital Rectal Exam (DRE) is a test that helps to identify cancer of the prostate, and should be performed on men who are 50 and older and to younger men at high risk for prostate cancer.

A biopsy is recommended for all men who have an abnormal PSA or DRE.

The options for primary management of prostate cancer are surgery, radiation therapy or close observation. Treatment decisions, are based on the aggressiveness of the cancer, the stage of the cancer and the life expectancy of the individual.

Advanced prostate cancer is best managed with hormone therapy.

Radiation therapy can include external and implanted seeds, a procedure known as brachytherapy.

The PSA test, which facilitates early detection of prostate cancer, has been available in Canada since 1986, although its use did not become widespread until the early 1990's. In 1994 the U.S. Food and Drug Administration (FDA) approved the use of the PSA test in conjunction with DRE as an aid in detecting prostate cancer. The free PSA test (fPSA), a more sensitive test for prostate cancer risk than the standard PSA test, received FDA approval in 1998.

Prostate Specific Antigen is an enzyme made by all prostate cells and normally secreted into semen. Both cancer and a number of benign conditions can change the architecture of the prostate gland so the enzyme escapes into the bloodstream. Once there, PSA can exist in two forms, one that is free-floating and another that is bound to proteins. The standard PSA test measures both forms. There are a number of specialized PSA tests which are used to help differentiate between elevated PSA due to benign conditions and those elevations due to prostate cancer. The free PSA test evaluates the ratio between the PSA that is free in the blood and the total PSA (free and protein bound PSA) in the blood. When the result of the free PSA test is low (i.e. <15%), there is a higher potential that the individual has prostate cancer. The PSA velocity is used to describe the speed at which the PSA value increases over a series of blood tests. The PSA density is used to evaluate the level of PSA in relation to overall size of the prostate gland.

The various PSA tests share some common limitations:

The principal concern is that although diagnostic accuracy has improved with each of the modifications to total serum PSA measurement, none of the forms is specific for prostate cancer.

Each requires a trade-off in specificity for increased sensitivity and vice versa. This trade-off appears to be most advantageous with the proportion of free PSA.

Elevation of PSA may indicate prostate cancer. However, several other common benign conditions, including Benign Prostatic Hyperplasia (BPH), are known to be associated with an elevated PSA.

Because of the limitations of the PSA test (lack of specificity for prostate cancer and a significant number of "false positive" and "false negative" test results) it remains an investigational tool as opposed to an absolute diagnostic test. Abnormal findings following the administration of the PSA test lead the investigator to perform a biopsy. Physicians are advised to consider a biopsy to confirm a prostate cancer diagnosis when a PSA test reading is at least 4.0 ng/mL, when the PSA level of an individual significantly increases from one test to the next, or when a DRE is abnormal. A biopsy is recommended for all men who have a PSA test result above 10 ng/mL.

The limitations of the PSA test are obvious considering the fact that only one of four individuals biopsied receives results that are positive for the presence of cancerous cells. A Canadian study has estimated the positive predictive value of the PSA test to be as low as 14.4%. This is significant considering the costs associated with a follow-up biopsy as well as the unnecessary pain and anxiety caused for individuals.

Since FDA approval in the U.S., the fPSA test is becoming a follow-up test for men whose PSA falls in a "diagnostic gray zone" of moderately elevated levels (4 to 10 ng/mL).

The digital rectal examination is a simple, inexpensive and direct method of assessing the prostate, but it is unreliable as a sole indicator of prostate cancer. The cancer detection rate is higher with PSA screening than with digital rectal examination (DRE), and the rate increases when the DRE modality is combined with PSA analysis and/or transrectal ultrasound examination (TRUS). DRE has never been shown to be reliable for, staging of prostate cancer. TRUS guided biopsy is required to follow-up on a positive PSA test in order to help confirm the presence or absence of disease in the individual's prostate.

Prostate biopsies are performed to confirm the presence of cancer cells following suspicion raised by the DRE or a positive PSA test. The most commonly reported complications of biopsy consist of traces of blood in the urine, semen or feces. These complications are limited and subside with 2-3 weeks after the procedure. Pain at the time of biopsy is universally reported. Only in exceptional cases is analgesia or sedation required. Most men (>90%) have no significant pain after 24 hours of the biopsy. Prostate biopsies are costly in the U.S. and may be painful or psychologically traumatic. Prostatic biopsy represents the cornerstone of prostate cancer diagnosis.

For prostate cancers in general, biopsies miss cancers at a rate estimated as high as 50 percent. Furthermore, even if a cancer is detected, the location and staging of cancerous cells are not adequately identified.

Thus, there is a need for an improved method for diagnosis and/or detection of cancerous prostate cells.

An important prognostic factor is prostate cancer stage. Cancer staging is performed to determine the extent and spread of cancer in the prostate. Prostate cancer metastasizes by local spread to the pelvic lymph nodes, seminal vesicles, urinary bladder, or pelvic side walls and to distant sites such as bone, lung, liver, or adrenals. The tumor-nodes-metastasis (TMN) staging system is the one most widely used in North America.

The limitations of the biopsy in detecting disease and staging a malignancy is compounded by the fact that prostate cancer is a heterogeneous disease with apparently independent foci of cancer scatter throughout the gland. The cancer foci have different malignant potentials and do not pose equal risks for the individual. Heterogeneity confounds the interpretation of positive prostate biopsies since it is not possible to be certain that the most clinically relevant foci of cancer have been detected.

Approximately only 30% of early stage disease will progress to clinically relevant disease within the lifetime of the individual. It is therefore critical to be able to identify those individuals at risk of progression who would benefit from aggressive therapy while sparing low-risk individuals the morbidity resulting from aggressive treatment of indolent disease. Neither rising PSA nor the presence of cancer cells on biopsy may indicate definitively the presence of lethal disease.

Serum PSA is a valuable cancer marker but cannot be used alone to determine the clinical or pathological stage of prostate cancer or to identify individuals with potentially curable disease. The combination of serum PSA with Gleason Score (a grading system for the classification of adrenocarcinoma of the prostate by observation of the pattern of glandular differentiation) and clinical stage provides a better prediction of the final pathologic stage than do any of these variables separately. Nomograms have been developed and revised to predict the final pathologic stage based on a combination of serum PSA level, Gleason Score, and clinical stage. Because these nomograms only offer a statistical probability of disease organ confinement, further radiographic evaluation has often been used for the individual. However, definitive detection of lymph node metastases with standard anatomical modalities of computed tomography (CT) and magnetic resonance imaging (MRI) has generally proved ineffective, except for the increasingly more uncommon cases with large volume soft-tissue involvement (greater than 1 cm) at presentation.

There is a great need for a new prostate imaging technology that provides for accurate visualization of extraprostatic growth indicative of metastasis. Such a technology would provide physicians with a tool to determine the progression of the cancer and would be extremely valuable in directing treatment options. Spectroscopy significantly improves the diagnosis of extracapsular extension by MRI. However, studies demonstrate that there is high variability in how clinicians interpret the significance of extracapsular extension. Both CT and MRI can be helpful in staging prostate cancer, because they can indicate periprostatic cancer spread, lymph node abnormality and bone involvement, but their sensitivity for revealing cancer extension has limitations.

Imaging techniques such as CT or MRI are unable to distinguish metastatic prostate cancer involvement of lymph nodes by criteria other than size (i.e. >1 cm). Thus, these imaging techniques, being inherently insensitive and non-specific, are insufficient for detection of disease.

The presence of pelvic lymph node metastasis influences both the treatment and the prognosis of individuals with prostate cancer. Lymph node involvement can be assessed surgically. However, incomplete sampling at the time of radical prostatectomy leads to false-negative interpretations in at least 12%, and possibly as many as 33% of individuals with lymph node metastases, because isolated metastases in the external iliac, presciatic, or presacral lymph nodes are outside the boundaries of the standard Pelvic Lymph Node Dissection.

Thus, there is a need for a non-invasive test that is able to identify lymph node metastases in individuals at risk for extraprostatic disease following the detection of elevated PSA and/or abnormal DRE and a positive biopsy. This will allow clinicians to reliably differentiate individuals with organ-confined disease from those with metastatic spread to lymph nodes. This will provide the opportunity for the individual and physician to make an informed decision on how to treat the disease and will significantly improve individual health outcome.

Despite considerable research into methods for therapy and disease treatment, prostate cancer remains difficult to treat. Current methods, commonly based on surgery and/or radiation therapy, are ineffective in a significant number of cases. Prostate surgery, for example, holds the potential for damaging nerve tissue and compromising an individual's chances of recovering sexual function. There is a need for an imaging technology that can help to minimize the risks involved in surgery by determining the location of both the cancer and the individual's normal structures.

Furthermore, a new technology that is able to localize cancerous prostate cells that remain following radical prostatectomy would assist physicians in removing all of the cancerous cells from an individual's body with focused treatment such as radiation therapy. A labeled technology that selectively binds prostate cancer cells will allow clinicians to localize any remaining cancer cells following surgery. An additional new technology would provide direct delivery of therapeutic agents, perhaps preventing the need for surgery.

Thus, there is a need for an improved method to detect and/or diagnose lymph node metastases in individuals at risk for extraprostatic disease following the detection of elevated PSA and/or abnormal DRE and a positive biopsy.

A substantial amount of work has been put into identifying enzyme or antigen markers, which could be used as sites for detection and/or diagnosis for various types of cancers. These markers could also be used to target cancer cells for treatment with therapeutic and/or cancer cell killing agents. The ideal cancer marker would exhibit, among other characteristics, tissue or cell-type specificity.

A 750 amino acid protein (FIG. 2; SEQ ID NO:22), prostate-specific membrane antigen (PSMA), localized to the prostatic membrane has been identified. The complete coding sequence of the gene (FIG. 1; nucleotides 262 to 2514 of GenBank™ accession number NM_004476) is presented as SEQ ID NO:22. PSMA is an integral Type II membrane glycoprotein with a short intracellular tail and a long extracellular domain. This antigen was identified as the result of generating monoclonal antibodies to a prostatic cancer cell, LNCaP (Horoszewicz et al. (1983) *Cancer Res.* 43:1809-1818). Israeli et al. (Israeli et al. (1993) *Cancer Res.* 53:227-230) describes the cloning and sequencing of PSMA and reports that PSMA is prostate-specific and shows increased expression levels in metastatic sites and in hormone-refractory states. Other studies have indicated that PSMA is more strongly expressed in prostate cancer cells relative to cells from the normal prostate or from a prostate with benign hyperplasia. Current methods of targeting prostate specific membrane antigen use antibodies with binding specificity to PSMA. One of the first antibodies described with binding specificity to PSMA was 7E11 (Horoszewicz et al. (1987) *Anticancer Res.* 7:927-936 and U.S. Pat. No. 5,162,504). Indium-labeled 7E11 localizes to both prostate and sites of metastasis, and is more sensitive for detecting cancer sites than either CT or MR imaging, or bone scan (Bander (1994) *Sem. In Oncology* 21:607-612).

One of the major disadvantages of the 7E11 antibody is that it is specific to the portion of the PSMA molecule which is present on the inside of the cell (intracellular). Antibody molecules do not normally cross the cell membrane, unless they bind to an extracellular antigen, which subsequently becomes internalized. As such, 7E11 can not be used to target a living prostate cell, cancerous or otherwise. The use of 7E11 for detection or imaging is therefore limited to pockets of dead cells within cancers or tissues with large amounts of dead cells, which cells render available their intracellular portion of PSMA for binding with this antibody.

U.S. Pat. No. 6,107,090, in the name of Neil Bander, and U.S. Pat. No. 6,150,508, in the name of Gerald Murphy et al. describe numerous monoclonal antibodies which recognize the extracellular domain of PSMA, thereby overcoming one of the major drawbacks of the 7E11 antibody. These antibodies, being able to bind to the extracellular domain of PSMA are capable of binding to living prostate cells, thereby allowing a more effective method of diagnosis than 7E11.

As described above, antibodies to PSMA are already in use for diagnostic purposes. For example, PSMA is the antigen recognized by the targeting monoclonal antibody used in ProstaScint™, U.S. Pat. Nos. 5,162,504 and 5,763,202, Cytogen's imaging agent for prostate cancer.

It would be highly desirable to be provided with an improved antibody specific for PSMA and a method for diagnosis and/or detection of cancerous prostate cells.

It would be highly desirable to be provided with a new prostate imaging technology offering accurate visualization of extraprostatic growth indicative of metastasis which would provide physicians with a tool to determine the progression of the cancer and be extremely valuable in directing treatment options.

It would be highly desirable to be provided with a non-invasive test that is able to identify lymph node metastases in individuals at risk for extraprostatic disease following the detection of elevated PSA and/or abnormal DRE and a positive biopsy.

It would be highly desirable to be provided with an imaging technology that decreases morbidity by identifying individuals in which surgery is not indicated.

It would be highly desirable to be provided with a new technology that is able to localize cancerous prostate cells that remain following radical prostatectomy which would assist physicians in removing all of the cancerous cells from an individual's body. In addition, it would be highly desirable to be provided with a new technology which would provide direct delivery of therapeutic agents, perhaps preventing the need for surgery.

It would be highly desirable to be provided with an improved method to detect and/or diagnose lymph node metastases in individuals at risk for extraprostatic disease following the detection of elevated PSA.

It would be highly desirable to be provided with a new prostate imaging technology that provides for accurate visualization of extraprostatic growth indicative of metastasis which would provide physicians with a tool to determine the progression of the cancer and be extremely valuable in directing treatment options.

It would be highly desirable to be provided with novel antibodies and their use for detecting, imaging, staging, treating and monitoring of prostate cancer, and/or metastasis thereof. It would also be highly desirable to be provided with novel pharmaceutical compositions for the treatment of prostate cancer.

SUMMARY OF THE INVENTION

One aim of the present invention is to provide novel antibodies and their use for detecting, imaging, staging, treating and monitoring of prostate cancer, and/or metastasis thereof.

Another aim of the present invention is to provide novel pharmaceutical compositions for the treatment of prostate cancer.

In accordance with one embodiment of the present invention there is provided an antigen comprising an epitope of the extracellular region of prostate specific membrane antigen (PSMA), ranging between amino acid 51 to amino acid 67, amino acid 85 to amino acid 102, amino acid 104 to amino acid 118, amino acid 161 to amino acid 173, amino acid 236 to amino acid 245, amino acid 278 to amino acid 288, amino acid 345 to amino acid 354, amino acid 490 to amino acid 500, amino acid 531 to amino acid 545, amino acid 551 to amino acid 567, amino acid 608 to amino acid 619, amino acid 649 to amino acid 660, amino acid 716 to amino acid 724, or amino acid 738 to amino acid 750 which comprises an amino acid sequence selected from the group consisting of SEQ ID NOs:1-14, respectively.

Preferably the antigen of the extracellular region of PSMA of the present invention is from a mammal, more preferably a human.

In accordance with another embodiment of the present invention there is provided a peptide selected from the group consisting of SEQ ID NOs:1-14.

In accordance with another embodiment of the present invention there is provided a recombinant nucleic acid molecule comprising a sequence which encodes a peptide of SEQ ID NOs:1-14, a variant or a fragment thereof.

A preferred recombinant nucleic acid molecule of the present invention is DNA.

A preferred recombinant DNA molecule of the present invention is operatively linked to an expression control sequence.

In accordance with another embodiment of the present invention there is provided an expression vector containing the recombinant DNA molecule.

In accordance with another embodiment of the present invention there is provided a method of expressing a recombinant DNA molecule in a cell containing the expression vector, comprising culturing the cell in an appropriate cell culture medium under conditions that provide for expression of the recombinant DNA molecule by the cell.

A preferred method of expressing a recombinant DNA molecule in a cell containing the expression vector further comprises the step of purifying a recombinant product of the expression of the recombinant DNA molecule.

In accordance with another embodiment of the present invention there is provided a unicellular host transformed with a recombinant DNA molecule for expression of a peptide of SEQ ID NOs:1-14, a variant or a fragment thereof.

In accordance another embodiment of with the present invention there is provided an immunogenic composition for raising antibodies specific to PSMA in a subject, which comprises a peptide selected from the group consisting of SEQ ID NOs:1-14 modified with an immunogenic moiety or carrier and/or an antigen of the present invention in association with a pharmaceutically acceptable carrier.

In a preferred immunogenic composition of the present invention the subject is an animal selected from the group consisting of mammals and birds, more preferably a human or a mouse, such as a BALB/c mouse, or a rabbit.

In a preferred immunogenic composition the immunogenic moiety or carrier is selected from the group consisting of keyhole limpet hemocyanin (KLH) and bovine serum albumin (BSA).

In accordance with another embodiment of the present invention there is provided a method of raising antibodies which bind to PSMA, which comprises administering an immunogenic amount of an immunogenic composition of the present invention, such as PSMA, an epitope of PSMA, or intact cell and/or fragment thereof exhibiting the extracellular region of PSMA, to an animal.

In accordance with another embodiment of the present invention there is provided a method of producing antibodies which bind to PSMA, comprising treating an animal with an immunogenic amount of an immunogenic composition of the present invention, such as PSMA, an epitope of PSMA, or intact cell and/or fragment thereof exhibiting the extracellular region of PSMA, to produce antibodies; and isolating the antibodies from serum of the animal.

In accordance with another embodiment of the present invention there is provided an isolated antibody or antigen binding fragment thereof, which binds to an antigen of the present invention.

A preferred isolated antibody or antigen binding fragment thereof of the present invention is a monoclonal antibody, such as a monoclonal antibody selected from the group consisting of F34-8H12, F42-3E11, F42-17G1, F42-29B4, F42-30C1 AND F47-20F2, or a polyclonal antibody.

The binding fragment may be selected from the group consisting of a Fab fragment, a F(ab')2 fragment, and a Fv fragment.

In accordance with another embodiment of the present invention there is provided a pharmaceutical composition for targeted treatment of prostate cancer, and/or metastasis with PSMA thereon, which comprises an antibody or binding fragment thereof according to the present invention bound to a cytotoxic drug in association with a pharmaceutically acceptable carrier, wherein the PSMA binding site of the antibody is available for targeted binding to PSMA and the bound cytotoxic drug remains biologically active.

In a preferred pharmaceutical composition of the present invention the cytotoxic drug is selected from the group consisting of iodine-125, iodine-131, cyclophosphamide, taxol, IFN-alpha and IL2 and/or mixtures thereof.

In accordance with another embodiment of the present invention there is provided a method for treating prostate cancer, and/or metastasis thereof comprising administering to an individual a pharmaceutically effective amount of a pharmaceutical composition according to the present invention.

In a preferred method of the present invention the administering is carried out orally, rectally, parenterally, subcutaneously, intravenously, intramuscularly, intraperitoneally, intraarterially, transdermally or by application to a mucus membrane.

In accordance with another embodiment of the present invention there is provided a composition for detection of prostate cancer, and/or metastasis thereof with PSMA thereon in an individual and/or in a sample obtained therefrom, which comprises an antibody or binding fragment thereof according to the present invention bound to a detectable label in association with a physiologically acceptable carrier or an in vitro acceptable carrier, wherein the PSMA binding site of the antibody is available for binding to PSMA and the detectable label remains detectable.

In a preferred composition of the present invention the detectable label is selected from the group consisting of a radioactive label, a fluorescent label, a nuclear magnetic resonance active label, a luminescent label, a chromophore label, a positron emitting isotope for PET scanner, chemiluminescence label, or an enzymatic label.

In accordance with another embodiment of the present invention there is provided a method of detecting prostate cancer cell, and/or metastasis thereof in an individual comprising administering to the individual an effective amount of a composition according to the present invention or subjecting a biological sample obtained from the individual to an effective amount of the composition according to the present invention and detecting the signal produced by the detectable label, wherein detection of the label above a certain level is indicative of the presence of prostate cancer, and/or metastasis thereof. A preferred method of the embodiment of present invention further comprises localizing a detectable label within the individual or a sample obtained therefrom.

In a preferred method of the present invention a 2-dimensional and/or 3-dimensional image of the individual or a sample obtained therefrom is generated.

In a preferred method of the present invention the method is used to indicate the location of prostate cancer, and/or metastasis thereof within the individual and/or sample obtained therefrom.

In accordance with another embodiment of the present invention there is provided an assay system for detecting prostate cancer, and/or metastasis thereof comprising a labeled antibody and/or antigen binding fragment thereof according to the present invention.

A preferred assay of the present invention further comprises means for semi-quantifying or quantifying an amount of antigen bound to the antibody and/or antigen binding fragment thereof, wherein an amount of antigen bound to the antibody and/or antigen binding fragment thereof above a predetermined level is indicative of prostate cancer, and/or metastasis thereof.

In a preferred assay of the present invention the assay is selected from the group consisting of immunoassay, enzyme linked immunosorbent assay (ELISA), array-based immunoassay, array-based ELISA.

A preferred assay of the present invention further comprises means for receiving the biological sample.

A preferred assay of the present invention further comprises a multi-well microplate including the antibody and/or antigen binding fragment thereof in at least one well.

In a preferred assay of the present invention the antibody and/or antigen binding fragment thereof binds to a peptide selected from the group consisting of PSMA, an extracellular region of PSMA, a peptide corresponding to an extracellular region of PSMA, an epitope of PSMA, and SEQ ID NOs:1-14.

In accordance with another embodiment of the present invention there is provided a method of determining relative efficacy of a therapeutic regimen to be performed on an individual suffering from and/or being treated for prostate cancer, and/or metastasis thereof, the method comprising: (a) initially analyzing the individual or a biological sample obtained therefrom to determine presence of cancer-associated antigen able to bind with the antibody and/or antigen binding fragment thereof according to the present invention; and (b) periodically repeating step (a) during treatment of the individual to determine an increase or decrease in quantity of cancer-associated antigen present in the sample.

In accordance with another embodiment of the present invention there is provided a method of determining the recurrence of a prostate cancer disease state in an individual clinically diagnosed as stabilized or in a remissive state, the method comprising analyzing the individual or a biological sample obtained therefrom to quantitate cancer-associated antigen immunoreactive with an antibody and/or antigen binding fragment thereof according to the present invention.

In accordance with another embodiment of the present invention there is provided a kit for detecting prostate cancer, and/or metastasis thereof comprising a composition according to the present invention.

In accordance with another embodiment of the present invention there is provided a hybridoma cell line that produces a monoclonal antibody which binds to an antigen of the extracellular region of PSMA, ranging between amino acid 51 to amino acid 67, amino acid 85 to amino acid 102, amino acid 104 to amino acid 118, amino acid 161 to amino acid 173, amino acid 236 to amino acid 245, amino acid 278 to amino acid 288, amino acid 345 to amino acid 354, amino acid 490 to amino acid 500, amino acid 531 to amino acid 545, amino acid 551 to amino acid 567, amino acid 608 to amino acid 619, amino acid 649 to amino acid 660, amino acid 716 to amino acid 724, or amino acid 738 to amino acid 750 which comprises an amino acid sequence selected from the group consisting of SEQ ID NOs:1-14, respectively.

For the purpose of the present invention the following terms are defined below.

The term "cancer" is intended to mean any cellular malignancy whose unique trait is the loss of normal controls which results in unregulated growth, lack of differentiation and ability to invade local tissues and metastasize. Cancer can develop in any tissue of any organ. More specifically, cancer is intended to include, without limitation, prostate cancer, leukemia, hormone dependent cancers, breast cancer, colon cancer, lung cancer, epidermal cancer, liver cancer, esophageal cancer, stomach cancer.

The term "prostate cancer" is intended to mean an uncontrolled (malignant) growth of cells in the prostate gland, which is located at the base of the urinary bladder and is responsible for helping control urination as well as forming part of the semen.

The term "metastasis" is intended to mean cancer that has spread beyond the prostate. "Metastasis" is also intended to mean the process by which cancer spreads from one part of the body to another, the way it travels from the place at which it first arose as a primary tumor to distant locations in the body.

The term "antibody" (Ab) is intended to mean intact antibody molecules as well as fragments, or binding regions or domains thereof (such as, for example, Fab, F(ab')2 and Fv fragments) which are capable of binding an antigen. Such fragments are typically produced by proteolytic cleavage, with enzymes such as papain or pepsin. Alternatively, antigen-binding fragments can be produced through recombinant DNA technology or through synthetic procedures.

The term "monoclonal antibody" (mAb) is intended to mean an antibody produced by a single clone of cells or a cell line derived from a single cell that has unique antigen binding characteristics or recognizes an individual molecular target. Such antibodies are all identical and have unique amino acid sequences.

The term "epitope" is intended to mean a molecular region on the surface of an antigen capable of eliciting an immune response and of combining with the specific antibody produced by such a response.

The term "cytotoxic compound" is intended to mean a compound, or molecule which is capable of killing a cell.

The term "detectable label" is intended to mean a label effective at permitting detection of a cell or portion thereof upon binding of a molecule to which the detectable label is attached to said cell or portion thereof. Alternatively, the detectable label permits detection of a cell upon internalization of the detectable label by the cell. A detectable label includes but is not limited to a radioactive label, a fluorescent label, a nuclear magnetic resonance active label, a luminescent label, a chromophore label, a positron emitting isotope for PET scanner, chemiluminescence label, or an enzymatic label.

The term "biological sample" is intended to mean a sample obtained from an individual and includes, but is not to be limited to, any one of the following: tissue, cerebrospinal fluid, plasma, serum, saliva, blood, nasal mucosa, urine, synovial fluid, microcapillary microdialysis.

The terms "treatment", "treating" and the like are intended to mean obtaining a desired pharmacologic and/or physiologic effect, such as inhibition of cancer cell growth or induction of apoptosis of a cancer cell. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes: (a) preventing a disease or condition (e.g., preventing cancer) from occurring in an individual who may be predisposed to the disease but has not yet been diagnosed as having it; (b) inhibiting the disease, (e.g., arresting its development); or (c) relieving the disease (e.g., reducing symptoms associated with the disease).

The terms "administering" and "administration" are intended to mean a mode of delivery including, without limitation, oral, rectal, parenteral, subcutaneous, intravenous, intramuscular, intraperitoneal, intraarterial, transdermally or via a mucus membrane. The preferred one being orally. One skilled in the art recognizes that suitable forms of oral formulation include, but are not limited to, a tablet, a pill, a capsule, a lozenge, a powder, a sustained release tablet, a liquid, a liquid suspension, a gel, a syrup, a slurry, a suspension, and the like. For example, a daily dosage can be divided into one, two or more doses in a suitable form to be administered at one, two or more times throughout a time period.

The term "therapeutically effective" is intended to mean an amount of a compound sufficient to substantially improve some symptom associated with a disease or a medical condition. For example, in the treatment of cancer, a compound which decreases, prevents, delays, suppresses, or arrests any symptom of the disease would be therapeutically effective. A therapeutically effective amount of a compound is not required to cure a disease but will provide a treatment for a disease such that the onset of the disease is delayed, hindered, or prevented, or the disease symptoms are ameliorated, or the term of the disease is changed or, for example, is less severe or recovery is accelerated in an individual.

The compounds of the present invention may be used in combination with either conventional methods of treatment and/or therapy or may be used separately from conventional methods of treatment and/or therapy.

When the compounds of this invention are administered in combination therapies with other agents, they may be administered sequentially or concurrently to an individual. Alternatively, pharmaceutical compositions according to the present invention may be comprised of a combination of a compound of the present invention, as described herein, and another therapeutic or prophylactic agent known in the art.

It will be understood that a specific "effective amount" for any particular individual will depend upon a variety of factors including the activity of the specific compound employed, the age, body weight, general health, sex, and/or diet of the individual, time of administration, route of administration, rate of excretion, drug combination and the severity of the particular disease undergoing prevention or therapy.

As used herein, "pharmaceutically acceptable carrier" includes any and all solvents (such as phosphate buffered saline buffers, water, saline), dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in therapeutic compositions is contemplated. Supplementary active ingredients can also be incorporated into the compositions.

BRIEF DESCRIPTION OF THE DRAWINGS

FIG. 1 illustrates the complete nucleotide coding sequence for human PSMA (nucleotides 262 to 2514 of Genebank accession number: NM_004476) (SEQ ID NO:21).

FIG. 2 illustrates the complete amino acid sequence (amino acid 1 to 750) of human PSMA (Genebank accession number: NP_004467) (SEQ ID NO:22).

FIG. 5 illustrates Western blot detection of PSMA by monoclonal antibodies of the present invention.

FIGS. 6A to 6D illustrate immunohistochemical staining of prostate tissue (cancer or normal) in accordance with the present invention.

DETAILED DESCRIPTION OF THE INVENTION

Figure 3:
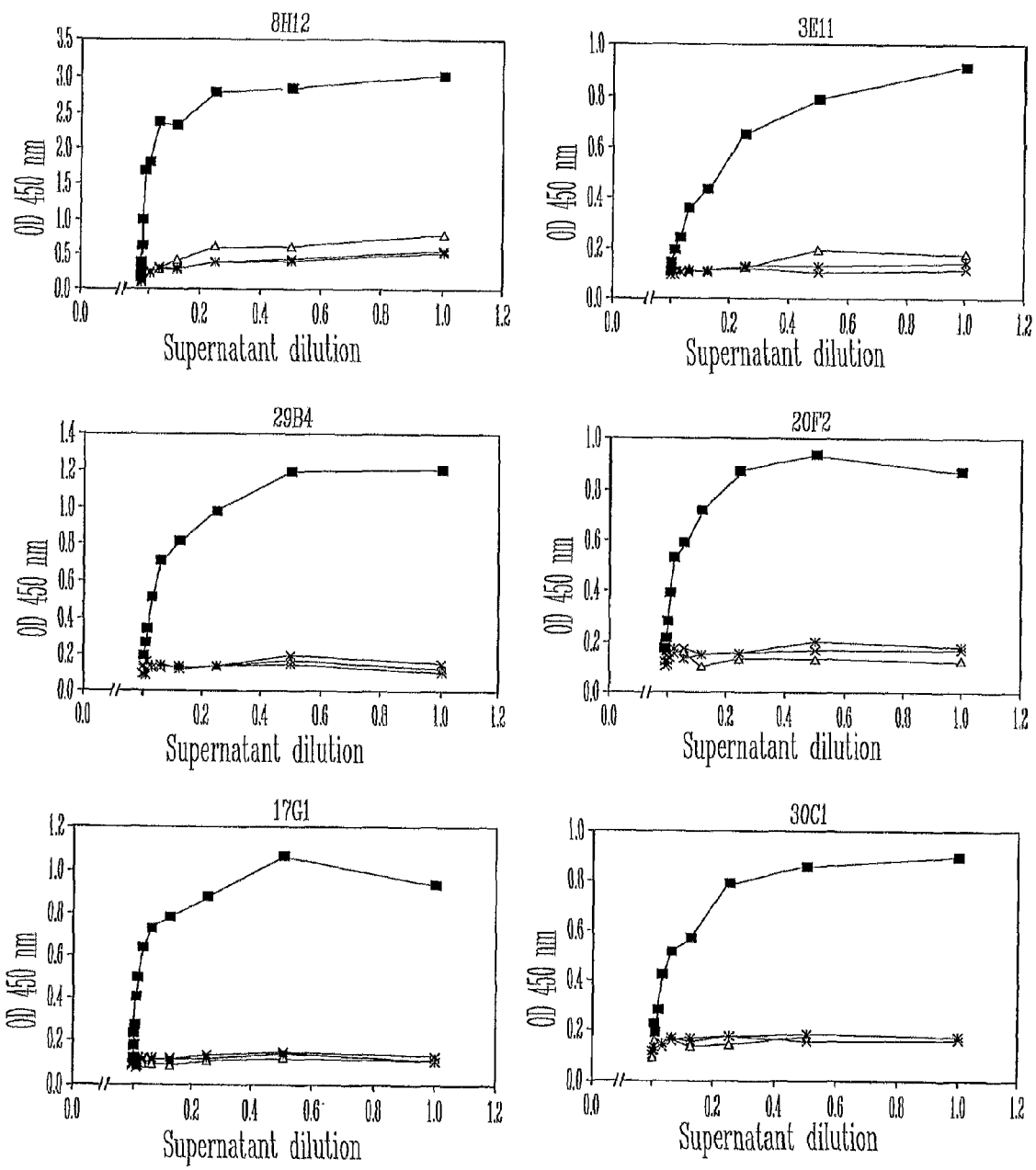
FIG. 3 illustrates reactivity of monoclonal antibodies of the present invention to LNCaP and various cells by ELISA.

In accordance with the present invention, there is provided epitopes of the extracellular region of prostate specific membrane antigen (PSMA), ranging between amino acid 51 to amino acid 67, amino acid 85 to amino acid 102, amino acid 104 to amino acid 118, amino acid 161 to amino acid 173, amino acid 236 to amino acid 245, amino acid 278 to amino acid 288, amino acid 345 to amino acid 354, amino acid 490 to amino acid 500, amino acid 531 to amino acid 545, amino acid 551 to amino acid 567, amino acid 608 to amino acid 619, amino acid 649 to amino acid 660, amino acid 716 to amino acid 724, or amino acid 738 to amino acid 750 which regions comprise an amino acid sequence selected from the group consisting of SEQ ID NOs:1-14, respectively.

Some epitopes were chosen based on hydrophilic character of the amino acid sequence (SEQ ID NO:22) and the lack of glycosylation consensus sites. Other sequences were selected from a rigorous analysis of PSMA secondary structure prediction and homology modeling with the most similar protein crystal structure (human transferrin receptor type 1). Regions were selected according to their apparent high solvent accessibility, flexibility, and coiled coil structure. In all cases the aim was to optimize antigenicity and sequence uniqueness such that antibodies raised against these peptides do not likely cross-react with other proteins.

In accordance with the present invention, there is provided a peptide corresponding to an epitope of the extracellular region of PSMA selected from the group consisting of SEQ ID NOs:1-14.

Small molecules such as the peptides of the present invention are incomplete immunogens. Although they are able to react specifically with antibodies, they are unlikely to induce an immune response when they are injected into an animal. In order to make them immunogenic in animals, small peptide sequences are covalently coupled to a carrier molecule, such as keyhole limpet hemocyanin (KLH) or bovine serum albumin (BSA). KLH and BSA are coupled to the peptides via a cysteine amino acid residue added to the N-terminus of the sequence of each peptide. The resulting peptide-conjugates are used to raise polyclonal and monoclonal antibodies.

In accordance with the present invention, there is provided an immunogenic peptide or recombinant peptide or protein for raising antibodies specific to PSMA, which comprises a peptide corresponding to an epitope of the extracellular region of PSMA modified with an immunogenic moiety or carrier.

In accordance with the present invention, there is provided a method for raising antibodies which bind to the epitopes and peptides of the present invention, which also have binding specificity to PSMA, such as PSMA in its native environment in LNCaP cells, or recombinant PSMA. The antibodies, or binding portions thereof, recognize and bind to PSMA in normal, benign, hyperplastic and cancerous prostate cells. Moreover, the antibodies, or binding portions thereof recognize and bind to PSMA in living normal, benign, hyperplastic and cancerous prostate cells. As a result of this binding, the antibodies or binding portions thereof are concentrated in areas with large numbers of prostate cells or portions thereof.

Antibodies in accordance with the present invention may be produced by procedures generally known in the art. For example, polyclonal antibodies may be produced by injecting the peptide or protein, such as PSMA or purified recombinant PSMA, alone or coupled to a suitable immunogenic moiety or carrier into a non-human animal. After an appropriate period, the animal is bled, sera recovered and purified by techniques known in the art. Monoclonal antibodies may be prepared, for example, by the Kohler-Milstein technique (1975, Nature 256(5517):497-497) involving fusion of an immune B-lymphocyte to myeloma cells. For example, antigen as described above can be injected into mice as described above until a polyclonal antibody response is detected in the mouse's sera. The mouse can be boosted again, its spleen removed and fusion with myeloma conducted according to a variety of methods. The individual surviving hybridoma cells are tested for the secretion of antibodies which bind the extracellular region of PSMA first by their ability to bind the immunizing antigen (peptide/protein). Monoclonal antibodies are produced in large quantities by growing the hybridoma clones in vitro or in vivo.

Serum from immunized and nonimmunized (control) animals are tested for the presence of specific antibodies in an Enzyme Linked ImmunoSorbent Assay (ELISA). For the ELISA assay each peptide is covalently coupled to a carrier molecule different than that used in the immunization phase of the procedure, or used uncoupled. Such a carrier molecule is, for example, bovine serum albumin (BSA): The same N-terminal cysteine of each peptide used to couple to the carrier molecule used for raising antibodies, for example KLH, is used to couple to the carrier molecule used for the ELISA, for example BSA. There are two reasons for this. First, immunization of animals with peptide-KLH induces the production of antibodies to both the peptide and KLH. Therefore, when screening for antibodies to the peptide it is important to eliminate the possibility of detecting binding to the KLH carrier by using peptide linked to a carrier the immunized mice have never seen. This eliminates background reactivity in the assay that may mask reactivity to the peptide of interest. Second, linking peptide to BSA in a similar manner as it was linked to KLH should permit antibodies induced to the peptide by immunization with peptide-KLH to recognize that peptide linked to the BSA carrier because its orientation is the same on each carrier surface.

The processes of the present invention encompass both whole antibodies and the binding portions thereof. Such binding portions thereof include Fab fragments, F(ab')2 fragments, and Fv fragments. These antibody fragments can be prepared by conventional procedures, such as proteolytic fragmentation as described in J. Goding, Monoclonal Antibodies: Principles and Practice, pp. 98-118, N.Y. Academic Press 1983.

Preferred monoclonal antibodies in accordance with one embodiment of the present invention are identified in Table 1 below. These antibodies were raised using peptide PSO215 (SEQ ID NO:8).

TABLE 1

Anti-PSMA Monoclonal Antibodies

| Monoclonal Antibody | isotype |
|---|---|
| F34-8H12 | $IgG_3$ K |
| F42-3E11 | $IgG_1$ K |
| F42-17G1 | $IgG_1$ K |
| F42-29B4 | $IgG_1$ K |
| F42-30C1 | $IgG_1$ K |
| F47-20F2 | $IgG_1$ K |

The antibody or binding portion thereof of the present invention can be used alone or in combination as a mixture with at least one other antibody or binding portion thereof with binding specificity for prostate antigen not herein described.

In accordance with the present invention there is provided a monoclonal antibody or binding fragment thereof which binds to an epitope of the extracellular region of PSMA ranging between amino acid 51 to amino acid 67, amino acid 85 to amino acid 102, amino acid 104 to amino acid 118, amino acid 161 to amino acid 173, amino acid 236 to amino acid 245, amino acid 278 to amino acid 288, amino acid 345 to amino acid 354, amino acid 490 to amino acid 500, amino acid 531 to amino acid 545, amino acid 551 to amino acid 567, amino acid 608 to amino acid 619, amino acid 649 to amino acid 660, amino acid 716 to amino acid 724, or amino acid 738 to amino acid 750 which regions comprise an amino acid sequence selected from the group consisting of SEQ ID NOs:1-14, respectively. Fourteen examples of peptides used to raise monoclonal antibodies developed using procedures described in detail below are presented in Table 2.

In accordance with the present invention, there is provided a monoclonal antibody or binding fragment thereof which binds to a peptide corresponding to an epitope of the extracellular region of PSMA selected from the group consisting of SEQ ID NOs:1-14.

In accordance with the present invention, there is provided a hybridoma cell line that produces a monoclonal antibody which binds to an epitope of the extracellular region of PSMA, ranging between amino acid 51 to amino acid 67, amino acid 85 to amino acid 102, amino acid 104 to amino acid 118, amino acid 161 to amino acid 173, amino acid 236 to amino acid 245, amino acid 278 to amino acid 288, amino acid 345 to amino acid 354, amino acid 490 to amino acid 500, amino acid 531 to amino acid 545, amino acid 551 to amino acid 567, amino acid 608 to amino acid 619, amino acid 649 to amino acid 660, amino acid 716 to amino acid 724, or amino acid 738 to amino acid 750 which regions comprise an amino acid sequence selected from the group consisting of SEQ ID NOs:1-14, respectively.

In accordance with the present invention there is provided a hybridoma cell line that produces a monoclonal antibody which binds to a peptide corresponding to an epitope of the extracellular region of PSMA selected from the group consisting of SEQ ID NOs:1-14.

The antibody or binding fragment thereof, or mixtures thereof may be unmodified or may be linked to 1) a radioimaging agent, such as those emitting radiation, for detection of the prostate cancer, and/or metastasis thereof upon binding of the antibody or binding fragment thereof, or mixtures thereof to the antigen, or 2) a cytotoxic agent, which kills the prostate cancer, and/or metastasis thereof upon binding of the antibody or binding fragment thereof, or mixtures thereof to the antigen. Alternatively, the cytotoxic agent is not toxic until internalized by the cell. Alternatively, the cytotoxic agent is toxic whether internalized or not internalized. Treatment is effected by administering the antibody or binding fragment thereof, or mixtures thereof to the individual under conditions which allow binding of the antibody or binding fragment thereof, or mixtures thereof to the antigen, and which binding results in the death of the cell of the prostate cancer, and/or metastasis thereof. In a preferred embodiment, administration is carried out on a living mammal. Such administration can be carried out orally or parenterally. In another embodiment the method is used to prevent or delay development or progression of prostate cancer, and/or metastasis thereof.

A cytotoxic agent of the present invention can be an agent emitting radiation, a cellular toxin (chemotherapeutic agent) and/or biologically active fragment thereof, and/or mixtures thereof to allow cell killing. A cytotoxic agent such as a cellular toxin and/or biologically active fragment thereof can be a synthetic product or a product of fungal, bacterial or other microorganism, such as mycoplasma, viral etc., animal, such as reptile, or plant origin. A cellular toxin and/or biologically active fragment thereof can be an enzymatically active toxin and/or fragment thereof, or can act by inhibiting or blocking an important and/or essential cellular pathway or by competing with an important and/or essential naturally occurring cellular component.

Cytotoxic agents emitting radiation for use in the present invention are exemplified by Yttrium-90 ($Y^{90}$), iodine-125 ($I^{125}$), iodine-131 ($I^{131}$) and gamma-emitting isotopes used, for example, to destroy thyroid tissue in some individuals suffering from hyperthyroidism.

Radioimaging agents emitting radiation (detectable radiolabels) for use in the present invention are exemplified by indium-111 ($In^{111}$), technitium-99 ($Tc^{99}$), or iodine-131 ($I^{131}$).

Detectable labels (non-radioactive labels) for use in the present invention can be a radioactive label, a fluorescent label, a nuclear magnetic resonance active label, a luminescent label, a chromophore label, a positron emitting isotope for PET scanner, chemiluminescence label, or an enzymatic label. Fluorescent labels are exemplified by fluorescein, and rhodamine. Chemiluminescence labels are exemplified by luciferase. Enzymatic labels are exemplified by peroxidase and phosphatase.

Cellular toxins and/or biologically active fragments thereof are exemplified by chemotherapeutic agents (anticancer cytotoxic compounds) known in the art, for example, cyclophosphamide and taxol. Biological compounds with cellular toxic effects are exemplified by Sapporin, *Pseudomonas exotoxin* (PE40), interferons (e.g. IFN-alpha) and certain interleukins (e.g. IL2).

In accordance with the present invention there is provided a pharmaceutical composition for targeted treatment of prostate cancer, and/or metastasis with PSMA thereon, which comprises an antibody or binding fragment thereof, or mixtures thereof bound to a cytotoxic agent in association with a pharmaceutically acceptable carrier, wherein the PSMA binding site of the antibody is available for targeted binding of PSMA and the cytotoxic agent remains biologically active.

In accordance with the present invention, there is provided a method of detecting normal, benign, hyperplastic and cancerous prostate epithelial cells, and/or metastases thereof in an individual or a biological sample obtained therefrom, i.e., the detection may be in vivo or in vitro. The method involves providing an antibody or binding fragment thereof or or mixtures thereof with binding specificity to an antigen of prostate cancer, or metastasis thereof. The antibody or binding fragment thereof or mixtures thereof is bound to a detectable label which upon binding of the antibody or binding fragment thereof or mixtures thereof allows detection of the prostate cancer, and/or metastasis thereof. Detection is effected by administering the antibody or binding fragment thereof or mixtures thereof to the individual or by contacting a biological sample obtained therefrom under conditions which allow binding of the antibody or binding fragment thereof or mixtures thereof to the antigen. Prostate cancer, and/or metastasis thereof is detected by monitoring of the signal produced by the detectable label above a predetermined base level, which indicates the presence of prostate cancer, and/or metastasis thereof. In a preferred embodiment, administration is carried out on a living mammal.

Detection of PSMA in, for example, a fluid sample obtained from an individual is an indication that prostate cells are being lyzed. Since PSMA is not present in the extracellular fluid of healthy individuals, the detection of PSMA in a biological sample from an individual is an indication of prostate cell lysis.

In a preferred embodiment detection of the signal produced by the detectable label is used in the generation of a 2-dimensional and/or 3-dimensional image of the individual or a biological sample obtained therefrom. In another preferred embodiment the 2-dimensional and/or 3-dimensional image is used to indicate the location of prostate cancer, and/or metastasis thereof within the individual or a biological sample obtained therefrom.

In accordance with the present invention there is provided a composition for targeted detection of prostate cancer, and/or metastasis thereof with PSMA thereon, which comprises an antibody or binding fragment thereof or mixtures thereof bound to a detectable label in association with a physiologically acceptable carrier, wherein said PSMA binding site of said antibody is available for targeted binding of PSMA and said detectable label remains detectable from inside or outside a cell.

In accordance with the present invention there is provided a method of detecting prostate cancer, and/or metastasis thereof in an individual or a biological sample obtained therefrom comprising: administering to the individual or a biological sample obtained therefrom an effective amount of a composition which comprises an antibody or binding fragment thereof or mixtures thereof bound to a detectable label in association with a physiologically acceptable carrier, wherein the PSMA binding site of the antibody is available for targeted binding of PSMA and the detectable label remains detectable from inside or outside a cell; and detecting the signal produced by the detectable label, wherein detection of the label above a certain level indicates the presence of prostate cancer, and/or metastasis thereof.

The antibody or binding fragment thereof or mixtures thereof with binding specificity to an antigen of prostate cancer, and/or metastases thereof of the present invention can be used and sold together with equipment, as a kit, to detect the particular label.

In accordance with the present invention there is provided an assay system for detecting prostate cancer, and/or metastasis thereof comprising: means for receiving a biological sample; means for detecting presence of antigen bound to at least one antibody or binding fragment thereof or mixtures thereof; and means for quantifying an amount of antigen bound to said at least one antibody or binding fragment thereof or mixtures thereof, wherein an amount of antigen bound to said at least one antibody or binding fragment thereof or mixtures thereof above a predetermined level indicates prostate cancer, and/or metastasis thereof.

In accordance with the present invention there is provided a method of determining the relative efficacy of a therapeutic regimen performed on an individual treated for prostate cancer, and/or metastasis thereof, the method comprising: initially analyzing an individual or a biological sample obtained therefrom to quantitate cancer-associated antigen able to bind with at least one antibody or binding fragment thereof or mixtures thereof; and periodically repeating the previous step during the course of application of the therapeutic regimen to determine increase or decrease in quantity of cancer-associated antigen present in the sample.

In accordance with the present invention there is provided a method of determining the recurrence of a prostate cancer disease state in an individual clinically diagnosed as stabilized or in a remissive state, the method comprising: initially analyzing an individual or a biological sample obtained therefrom to quantitate cancer-associated antigen immunoreactive with at least one antibody or binding fragment thereof or mixtures thereof; and periodically repeating the previous step during the course of application of the therapeutic regimen to determine increase or decrease in quantity of cancer-associated antigen present in the sample.

Regardless of whether the antibody or binding fragment thereof, or mixtures thereof of the present invention is used for treatment, detection, or imaging, it can be administered orally, parenterally, subcutaneously, intravenously, intramuscularly, intraperitoneally, by intranasal instillation, by intracavitary or intravesical instillation, intraocularly, intraarterially, intralesionally, as an aerosol, or by application to mucous membranes, such as, that of the nose, throat, and bronchial tubes. It may be administered alone or with a pharmaceutically or physiologically acceptable carrier, excipient, or stabilizer, and can be in solid or liquid form such as, tablet, capsule, powder, solution, suspension or emulsion.

The treatment and/or therapeutic use of the antibody of the present invention can be used in conjunction with other treatment and/or therapeutic methods. Such other treatment and/ or therapeutic methods include surgery, radiation, cryosurgery, thermotherapy, hormone treatment, chemotherapy, vaccines, other immunotherapies, and other treatment and/or therapeutic methods which are regularly described.

In addition to methods of treatment and/or therapeutic use, the antibodies of the present invention, by their binding positions on the PSMA protein, can be used for epitope mapping of the architecture of the PSMA protein in epitope mapping studies. The antibodies of the present invention can also be used as probes for screening a library of molecules, agents, proteins, peptides and/or chemicals to identify a molecule, agent, protein, peptide and/or chemical. Such a library could be a chemical library, antibody library, phage display library, peptide library or library of natural compounds. The identified molecule, agent, protein, peptide and/or chemical could be an antagonist or agonist of PSMA.

The present invention will be more readily understood by referring to the following examples which are given to illustrate the invention rather than to limit its scope.

Example 1

Peptide Synthesis

Example 1 relates to the procedures whereby peptides corresponding to epitopes of the extracellular domain of PSMA are synthesized.

Table 2 shows the sequence and their location within the PSMA amino acid sequence of the 14 peptides that were synthesized by solid phase F-MOC chemistry to greater than 85% purity. Each peptide was synthesized with a single amino terminal unblocked cysteine residue. This amino acid was used to conjugate each peptide to lysine residues in KLH and bovine serum albumin (BSA) carrier proteins using N-maleimide chemistry.

TABLE 2

Sequence of synthesized peptides

| Reference No. | Peptide Sequence[a] | Location | SEQ ID NO |
|---|---|---|---|
| 4243 | $NH_2$-CNITPKHNMKAFLDELKA | 51-67 | 1 |
| 4244 | $NH_2$-CGTEQNFQLAKQIQSQWKE | 85-102 | 2 |
| PS0210 | $NH_2$-CGLDSVELAHYDVLLS | 104-118 | 3 |
| PS0211 | $NH_2$-CFSAFSPQGMPEGD | 161-173 | 4 |
| PS0212 | $NH_2$-CAPGVKSYPDG | 236-245 | 5 |
| PS0213 | $NH_2$-CAYRRGIAEAVG | 278-288 | 6 |
| PS0214 | $NH_2$-CHIHSTNEVTR | 345-354 | 7 |
| PS0215 | $NH_2$-CGKSLYESWTKK | 490-500 | 8 |
| 4245 | $NH_2$-CASGRARYTKNWETNK | 531-545 | 9 |
| 4246 | $NH_2$-CLYHSVYETYELVEKFYD | 551-567 | 10 |
| PS0216 | $NH_2$-CADKIYSISMKHP | 608-619 | 11 |
| PS0217 | $NH_2$-C-CSERLQDFDKSNPIVLR-C | 649-660 | 12 |
| PS0218 | $NH_2$-CESKVDPSKA | 716-724 | 13 |
| PS0219 | $NH_2$-CTVQAAAETLSEVA | 738-750 | 14 |

[a]N-terminal C residues on each peptide are optionally added for manipulation and/or coupling; they are not part of the PSMA sequence. The C residues at the N-terminal and C-terminal of PS0217 also allow for the potential for cyclization.

Example 2

Preparation of Monoclonal Antibodies

Example 2 relates to preparation of mouse monoclonal antibodies with specificity to the peptides of Example 1.

Several strategies were used to immunize BALB/c mice for production of PSMA-specific antibodies.

One strategy consisted of priming and boosting at 2 to 3 week intervals with peptide conjugated to KLH by one of 2 methods that link the amino terminal cysteine of the peptide immunogen to lysine residues on KLH. Peptides were conjugated to KLH using either sulfo-GMBS or SMCC conjugation systems. This strategy was designed to induce and amplify peptide specific antibodies.

A second strategy employed 2 immunizations at 2 to 3 week intervals with LNCaP membrane followed by 3 immunizations with purified PSMA or peptide conjugated KLH. Priming with LNCaP membrane should induce the production of an antibody response directed to membrane antigens including PSMA presented in a native conformation within a cellular membrane. Boosting with purified PSMA antigen should further activate and expand the B lymphocyte clones secreting antibody that recognizes epitopes present on whole native PSMA whereas boosting with peptide conjugated KLH should further activate and expand the B lymphocyte clones recognizing the epitopes corresponding to the peptide used in the boost immunizations.

All immunizations were intraperitoneal injections of 100 μl volumes containing 25 to 50 μg of peptide antigen or 50 μl of LNCaP membrane preparation. The antigen for the first immunization was emulsified in complete Freund's adjuvant (CFA). Antigen used for subsequent immunizations were emulsified in incomplete Freund's adjuvant (IFA). The final boost before fusing donor spleen with the NS0 myeloma parental cell line was done 3 to 5 days before fusion. For this immunization antigen was diluted in phosphate buffered saline (PBS).

The fusion was performed according to the technique known in the art (Kohler G. and Milstein C. (1975) Nature 256 (5517):495-97).

Supernatants of the resulting wells exhibiting growth were screened by Enzyme Linked Immunosorbent Assay (ELISA) for the presence of antibodies binding to peptide (conjugated or not to BSA) and either LNCaP cell membranes or recombinant PSMA. Negative controls for the screening step were BSA alone (control for peptide or PSMA binding) or PC-3 cell membrane (control for LNCaP binding). Wells containing antibodies with desirable binding characteristics were subjected to at least 2 cycles of cloning by limiting dilution. Hybridomas secreting either one of the 6 monoclonal antibodies against peptide PSO215 (SEQ ID NO:8) were generated according to this screening strategy. The isotype of the immunoglobulin secreted into cultured supernatants by cloned antibody secreting hybridomas was determined using Isostrips (Roche Diagnostics Corp., Indianapolis Ind.).

Example 3

Preparation of Cell Membrane and Purified PSMA

Cell Membrane Preparation

Example 3 relates to the purification of recombinant PSMA and cell membrane for immunization and characterization of mAb.

LNCaP cells (ATCC No. ERL-1740), PC3 (ATCC No. CRL 1435 KS62 (ATCC No. CCL 243), NMB7 (Gift from Dr. U. Saragovi) were grown at 37° C. in RPMI-1640 supplemented with 10 mM HEPES, 10% FCS, 30 μg/ml kanamycin, 200 μg/ml streptomycin, and 20 μg/ml neomycin, and 2 mM L-glutamine, under a humidified atmosphere of 5% $CO_2$. When confluent, cells were washed with PBS and detached using 1 mM EDTA in PBS. Cells were spun down and the pellet frozen. Packed cells were resuspended in 10 volumes of ice cold hypotonic buffer (5 mM Tris pH 7.6; 2 mM EDTA) containing protease inhibitors (20 μg/ml of TLCK lysine chloromethyl ketone) 20 μg/ml TPCK (N-tosyl-1-phenylalanine chloromethyl ketone) and 20 μg/ml PMSF (phenylmethyl sulfonyl fluoride). Cells were sonicated using a probe sonicator at medium setting with three 30-second bursts on ice. Sonicated cells were centrifuged at 1500×g for 10 min at 4° C. Supernatant was collected and centrifuged at 12,000×g for 60 min at 4° C. The membrane pellet was resuspended in 10 volumes of the following buffer (250 mM sucrose, 50 mM Tris-HCl pH7.4, 5 mM EDTA, 100 mM NaCl) and frozen until use.

Cloning of PSMA from LNCaP Cells

Total RNA from LNCaP was isolated using the Trizol method according to manufacturer's directions (GIBCO Life Technologies Inc.) and treated with DNase I (RNase free). LNCaP RNA was reverse transcribed by Thermoscript reverse transcriptase and oligo dT primers (GIBCO Life Technologies Inc.). DNA corresponding to the gene encoding PSMA was then amplified by PCR using the oligonucleotides (5'3') ATGTGGAATCTCCTTCACGAAACC (SEQ ID NO:15) and TTAGGCTACTTCACTCAAAGTCTC (SEQ ID NO:16). The resulting PCR product was cloned into plasmid pCRT7-NT. Clones were sequenced to verify the identity of the insert DNA as originating from PSMA.

Baculovirus Expression of PSMA

PSMA was PCR-amplified from a sequence-confirmed recombinant plasmid of pCRT7-NT using primers GGG-GATCCATGTGGAATCTCCTTCACG (SEQ ID NO:17) and GGGCTCGAGGGCTACTTCACTCAAAGTCT (SEQ ID NO:18) (full length PSMA, flPSMA) or the oligonucleotides GGGGATCCGAAATCCTCCAATGAAGC-TACTAAC (SEQ ID NO:19) and GGGCTCGAGTTAGGC-TACTTCACTCAAAGTCTC (SEQ ID NO: 20) (soluble PSMA, sPSMA). The PCR fragment was digested overnight with the restriction enzymes BamHI and XhoI and cloned into Novagen transfer vector pBAC-1 (flPSMA) or pBAC-3 (sPSMA). The recombinant virus encoded either a full length PSMA containing a C-terminal poly-histidine tag or a truncated PSMA containing a poly-histidine tag at the N-terminus. Sf9 cells were co-transfected with the transfer vector DNA and the linearized viral DNA according to the manufacturer's directions. The viruses were plaque purified prior amplification to obtain a high titer viral stock.

Sf9 cells were propagated in TNM-FH medium supplemented with 10% fetal bovine serum, 0.1% Pluronic F-68 (InVitrogen), and the antibiotics kanamycin (30 ug/ml), neomycin (20 ug/ml) and streptomycin (200 ug/ml). Infection of Sf9 cells with recombinant baculovirus was done at a multiplicity of infection of about 10. After 3 days post-infection. flPSMA was solubilized from a cell lysate (PBS containing 1% Triton X-100) and secreted sPSMA was recovered directly from the medium. Both proteins were purified by affinity chromatography using a Ni-NTA resin, according to the manufacturer's instruction (Qiagen). The eluate was dialysed extensively against PBS before use as an immunogen or for hybridoma screening.

Example 4

Characterization of Monoclonal Antibodies

Monoclonal Antibodies Reactivity to PSMA by ELISA

Example 4 relates to the characterization of the mAbs by ELISA, western blot IHC, and in vivo biodistribution.

mAb reactivity to PSMA was assayed by ELISA. The LNCaP cell line was used as a source of natural PSMA and various PSMA non-expressing cell line as negative control. 5 ug of cell membrane preparation in 100 ul PBS were adsorbed onto 96 well plates (Immulon 2HB, Thermo Labs System) overnight at 4° C., or 2 hours at room temperature. The plates were washed with TBST (10 mM Tris-HCl pH 7.5, 150 mM NaCl, 0.05% Tween-20) then incubated with TBST containing 3% casein for 1 hours to block non-specific sites. The wells were loaded with 100 ul of the hybridoma cell supernatants or a dilution in TBST, and incubated for 1 hour at room temperature under gentle agitation. In some cases, the mAb was pre-mixed with dilutions of the antigenic peptide or an irrelevant peptide and then the solution applied to coated cell lysate. The plates were washed with TBST then incubated for 1 hour with a horse-radish peroxidase conjugated goat anti-mouse IgG (Jackson #115-035-164) secondary antibody at a dilution 1/1000 in TBST. After extensive washing, the plates were incubated with 100 ul of the peroxidase substrate TMB (BioFX). The reaction was stopped with an equivalent volume of 0.5N sulfuric acid and the reactivity evaluated by reading at OD 450 nm.

FIG. 3 shows a representative reactivity of the six monoclonal antibodies for the LNCaP cells (-□-) compared to the PSMA negative human cancer cell lines PC-3 (prostate, -▲-), K562 (myeloid leukemia, -x-) and NMB-7- (neuroblastoma, -Δ-). The graph illustrates that only a very weak signal was detected from the negative control cell lines as compared to the strongly reactive LNCaP cells. Indeed, the average reactivity (±SEM) of the antibodies to LNCaP over PC-3 background was found to be 9.0±3.6 for the 8H12 (n=8), 25.7±6.3 for the 3E11 (n=7), 26.1±6.32 for the 29B4 (n=8), 10.9±3.0 for the 30C1 (n=5), 16.9±4.4 for the 17G1 (n=5), and 58.9±15.6 for the 20F2 (n=4). These results suggest that the reactivity of the mAbs is specific for a protein expressed by the LNCaP cells only.

Figure 4:
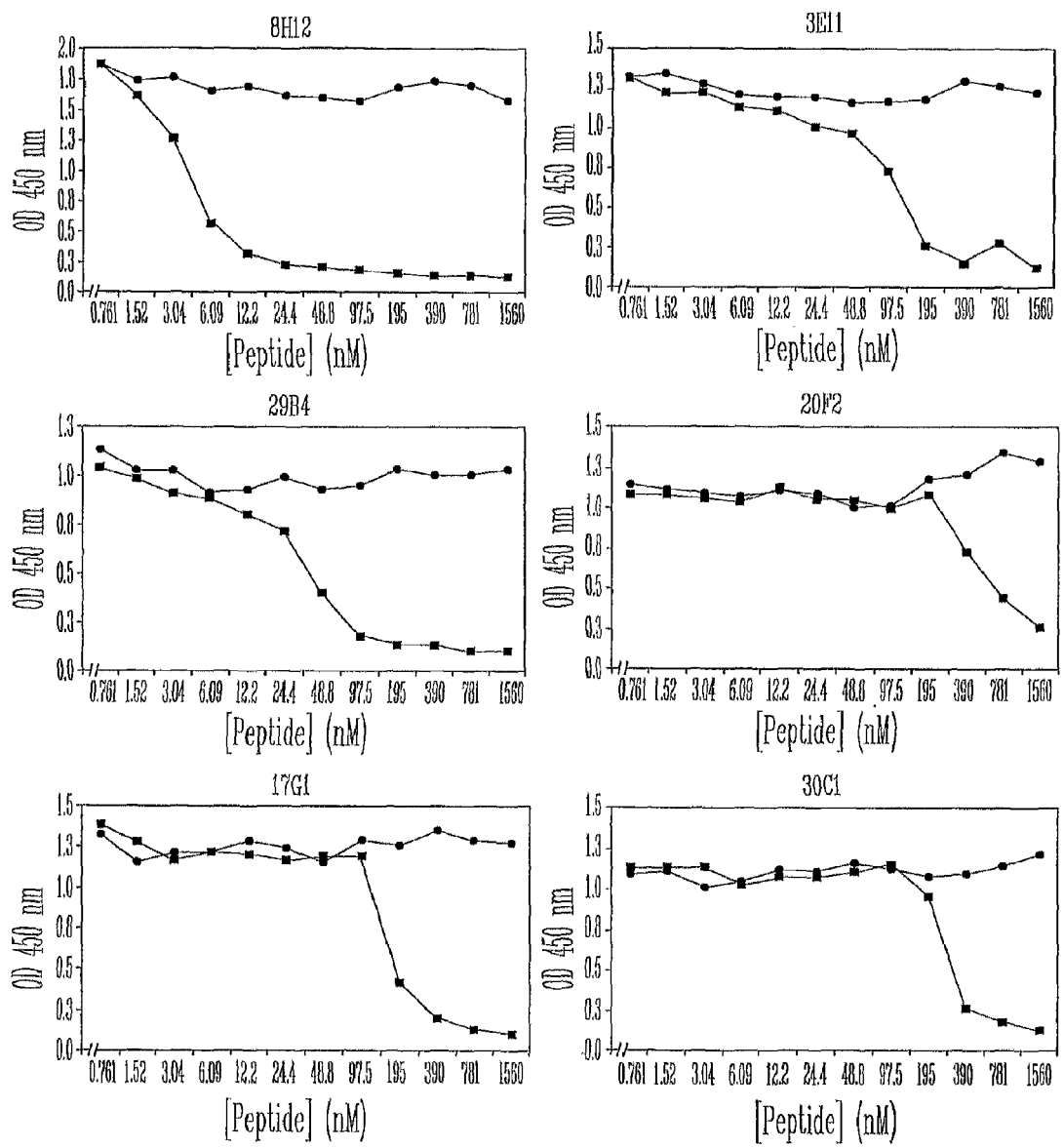
FIG. 4 illustrates the specificity of monoclonal antibodies of the present invention to PSMA derived antigen peptides.

In order to confirm the specificity of the mAbs, the reactivity of the mAbs to LNCaP cells were challenged by the original antigen from which they were generated (PS0215) (SEQ ID NO:8). FIG. 4 shows that nanomolar concentrations of the antigenic peptide PS0215 (-□-) can completely inhibits the binding of the antibodies to LNCaP cells. In contrast, no change in the reactivity of the antibodies were observed when challenged with up to micromolar concentration of another peptide derived from the PSMA amino acid sequence (PS0210, -○-). The results suggests that the antibodies recognize a unique linear amino acid sequence of PSMA (PS0215) i.e. corresponding to PS0215 or SEQ ID NO:8.

Western Blot Detection of PSMA

Western Blot analysis were performed on LNCaP and PC-3 cell membrane in order to confirm that the mAbs detect the PSMA protein. Proteins from 2.5 ug of a cell membrane preparation were separated by SDS-polyacrylamide gel electrophoreisis on a 7.5% gel. The proteins were then transferred to a PVDF membrane and the membrane was blocked with 3% casein in TBST (10 mM Tris-HCl pH 7.5, 150 mM NaCl, 0.05% Tween-20) for 1 hour at room temperature. After washing, the membrane was incubated with the hybridoma supernatant diluted 1/1000 in TBST, and incubated 1 hour under gentle agitation. After extensive washing with TBST, the membrane was incubated with a 1/5000 dilution of horse-radish peroxidase conjugated goat anti-mouse IgG (Jackson #115-035-164) secondary antibody for 1 hour. After washing, the membrane was developed with a chemiluminescent substrate according to the manufacturer's recommendations (Pierce #34080).

FIG. 5 shows that all mAbs detected a single band of a molecular weight of about 100 KDa in LNCaP cell membrane (lane 1) and not in the PC-3 cell membrane (lane 2). The fact that the antibodies detected a band from a reducing and denaturing gel also confirm that they recognise a linear amino acid sequence of PSMA as opposed to a conformational epitope.

Immunohistochemical Staining of Prostate Cancer Tissue

Immunohistochemical staining was performed on paraffin embedded section from prostate cancer. After deparafinization and rehydration through graded alcohol, endogenous peroxidase was inactivated by treating sections with 3% $H_2O_2$ for 20 min at RT. Non specific binding was blocked with 5% normal goat serum (NGS) in 0.01M phosphate buffered saline pH 7.4; 0.05% Triton (PBS-T) for 30 min at RT before adding primary antibodies diluted in PBS-T; 2% NGS overnight at RT. 8H12 was used as a tissue culture supernatant diluted 1:5. Mouse IgG with an irrelevant specificity was used as a negative control at a concentration of 2 µg/ml. After washing, binding of primary antibody to tissue sections was detected by sequential addition followed by washing of goat anti-mouse Ig heavy+light chain polyclonal antibody (ICN) at 1:100, a complex of horse radish peroxidase (HRP, 5 µg/ml) and a mouse monoclonal antibody engineered to have dual specificity for goat antibody and HRP (1/30), and DAB (0.06%); 0.01% $H_2O_2$ all diluted in PBS-T; 2% NGS. Sections were washed in tap water, counterstained with hematoxylin and rinsed in tap water. Sections were then dehydrated and mounted in Permount™ (Sigma). A pathologist evaluated all immunohistochemical sections in a blinded fashion.

Figure 6A:
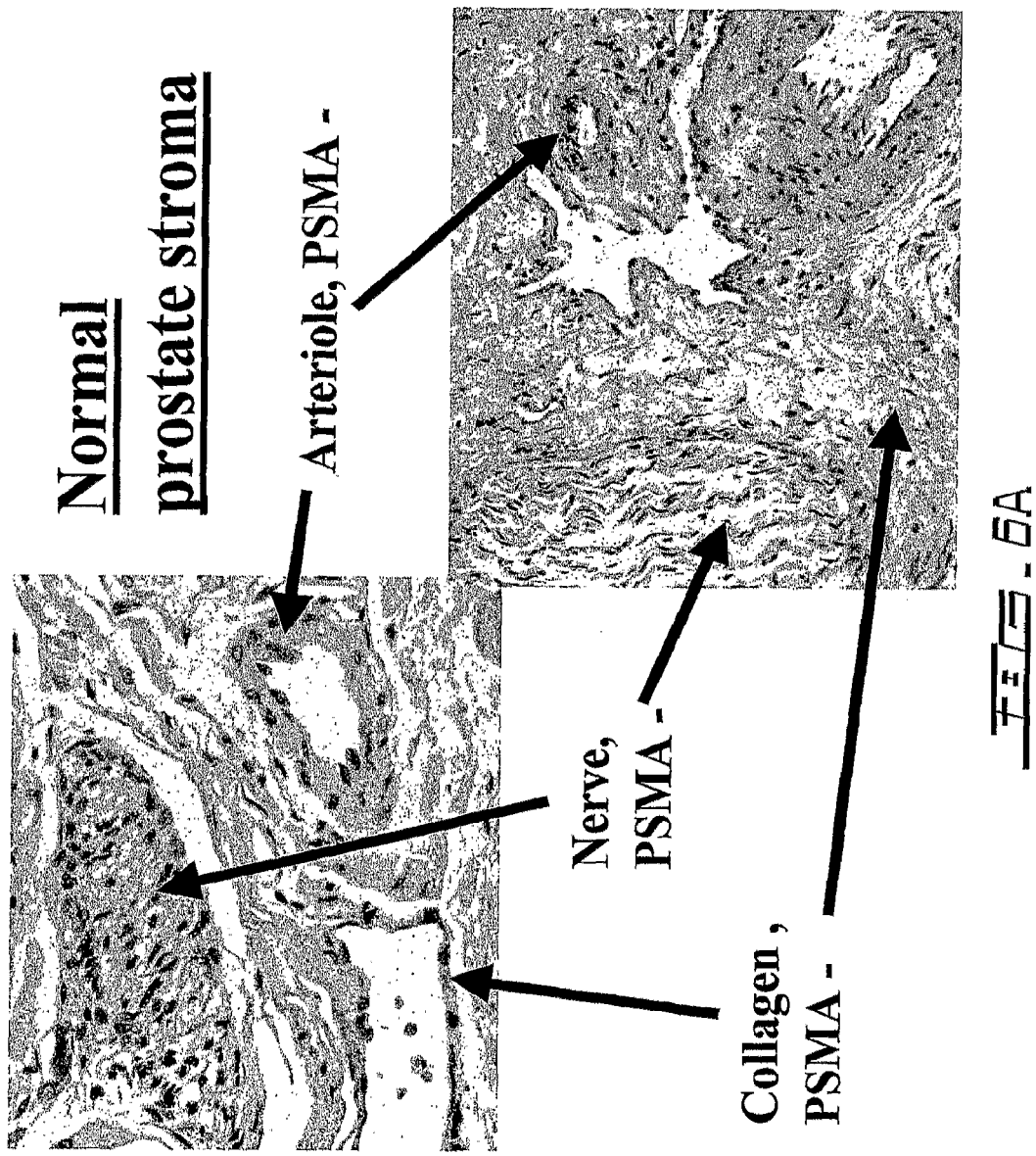

FIGS. 6A to D show paraffin embedded sections of prostate tissue from patients diagnosed with prostate cancer, stained immunohistochemically with the mAb 8H12. Shown are results for non antigen retrieved material. While 8H12 bound PSMA focally in prostate epithelial cells of both benign and malignant prostate tissue, normal structures in the prostatic stroma, nerve tissue, smooth muscles of blood vessel walls and collagen, were negatively stained for PSMA (FIG. 6A). As well, inflammatory cells (not shown) and endothelial cells stain negatively.

Staining of the benign prostatic glands, composed of prostatic acinar cells and underlying basal cells, show that the basal cells are PSMA negative, whereas the acinar cells are PSMA positive, mainly at the luminal aspect of the plasma membrane (FIGS. 6B, C and D). 8H12 shows moderate staining of PSMA in well differentiated prostate cancer, i.e. Gleason 3+3=6. Weaker cytoplasmic staining is also seen.

In Vivo Biodistribution of Labeled Anti-PSMA mAbs

Purification of mAb:

Cells were grown in Iscove's medium, 20% FCS, IL-6 (1 mg/ml), and antibiotics using T175 flasks. After reaching confluence, cells were removed by centrifugation. The medium was precipitated with saturated ammonium sulfate (final concentration=45%) overnight at 4° C. The solution was centrifuged and the supernatant discarded. The precipitate was resuspended in PBS pH 7.4 and further dialyzed against PBS at 4° C. A 5 ml protein G column (Amersham) was equilibrated with 20 mM $NaH_2PO_4$ pH 7.0 and the Ab solution was then passed through using a syringe barrel. The column was washed with 20 mM $NaH_2PO_4$ pH 7.0 and finally elution was done using Pierce's ImmunoPure Gentle Ag/Ab Buffer. Fractions containing the Ab were combined and buffer exchanged into PBS using Amicon Centriplus filtration devices.

Labelling of mAbs:

100 ug mAb were labelled by the method of chloramine T (Bioconjugate Techniques (1996) Elsevier Science (USA)) by mixing about 10 mCi $NaI^{125}$ and five fold antibody molar equivalent of chloramine T in a total volume of 135 ul. After 30 seconds, the reaction was quenched with 100 ul sodium meta-bisulfite at a concentration of 2.6 mg/ml. Free $I^{125}$ was removed by gel filtration of the antibody solution in a sodium phosphate buffer containing 0.1% BSA. 85% to 92% of the radioactive iodine was associated with the antibody, as assessed by HPTLC.

In Vivo Biodistribution of Labelled Anti-PSMA mAbs

In vivo targeting potential of the $I^{125}$-8H12 and $I^{125}$-29B4 was assessed in nude mice bearing LNCaP and/or PC3 tumors. Nude mice were injected subcutaneously in the flank with $0.5 \times 10^6$ trypsinized LNCaP cells and/or in the other flank with PC-3 cells in a volume of 200 ul PBS containing 50% Matrigel (Becton Dickinson). 1 month after the cell injection, the mice were administered, by tail vein injection, 2 or 20 ug of the mentioned labelled mAb at a specific activity of ~2 uCi/ug. After 24 or 48 hours post-injection, the mice were sacrificed and the tumors and major organs were recovered and cleaned from blood. A blood sample was also obtained at the time of sacrifice. The blood and tissue samples were weighted and counted for radioactivity incorporation in a gamma counter.

The relative activity of the tissue (cpm) was expressed per mg of tissue. For mice bearing both LNCaP and PC-3 tumors, the ratio of the relative activity of LNCaP/PC-3 tumor was calculated. For comparison of mAb uptake between mice, relative tissue activity was first normalized to blood to account for difference in the efficiency of injection, and then the ratio of the relative activity of LNCaP tumor over non tumor tissue was calculated.

Figure 7:
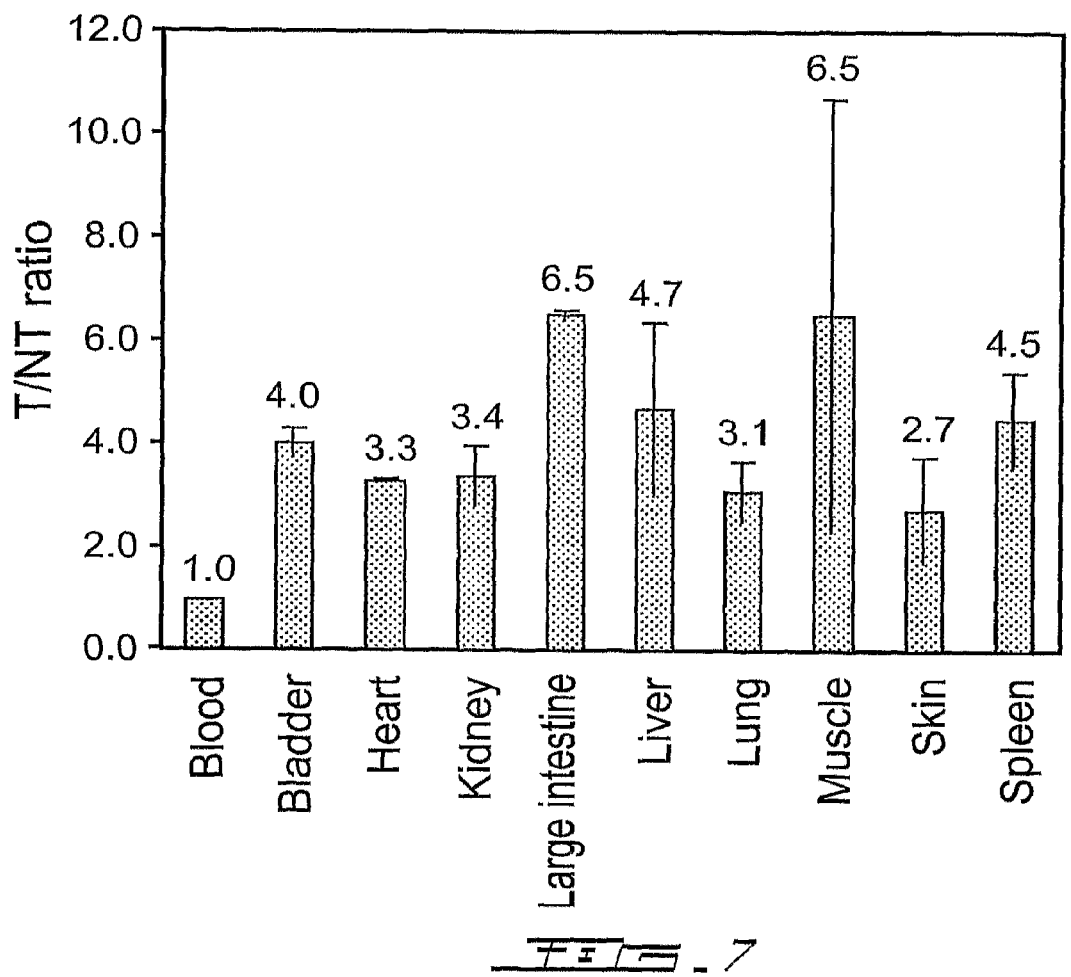
FIG. 7 illustrates Bio-distribution of monoclonal antibody of the present invention (8H12) in nude mice bearing LNCaP tumor.

FIG. 7 shows the LNCaP retention potential of the labeled Ab over normal tissue 48 hrs after an injection. The LNCaP tumor retained the labelled 8H12 antibody between 2.7 and 6.5 times better than the various tissues tested. The tissue retention was comparable at 24 h post-injection, indicating a complete bio-distribution of the mAb in a minimum of 24 h. These results indicate a significant concentration of 8H12 in LNCaP tumor compared to major organs.

The selectivity of the 8H12 and 29B4 for LNCaP tumor compared to PC-3 tumor was also measured in mice bearing both type of cells. Table 3 shows that 2 ug of the labelled 8H12 resulted in the concentration of the mAb 4.3 times higher than in the PC-3 tumor.

TABLE 3

In vivo tumor selectivity of anti-PSMA mAb
LNCaP/PC-3 tumor ratio, 48 hrs post injection

|  | mAb | Ratio |
|---|---|---|
| 2 µg | 8H12 | 4.3 |
| 20 µg | 29B4 | 2.7 |

20 ug of the mAb 29B4, also revealed a significant concentration (2.7 times) in LNCaP tumor compared to PC-3.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method of detecting prostate cancer and/or metastases thereof in a mammal comprising:
   a) administering to said mammal an antibody or antigen binding fragment which specifically binds to a peptide consisting of SEQ ID NO: 8 and which specifically binds to an epitope of a prostate specific membrane antigen (PSMA) polypeptide comprising SEQ ID NO: 22 or contacting a biological sample obtained from said mammal with the antibody or antigen binding fragment thereof; and
   b) detecting the antibody or antigen binding fragment thereof or a signal produced by a detectable label attached to said antibody or antigen binding fragment thereof.

2. The method according to claim 1, wherein said mammal is a mouse or human.

3. The method according to claim 1, wherein said antibody or antigen binding fragment thereof is a monoclonal antibody.

4. The method of claim 1, wherein said detecting allows localization of said detectable label within said mammal or sample obtained therefrom.

5. The method of claim 4, wherein a 2-dimensional and/or 3-dimensional image of said mammal or sample obtained therefrom is generated.

6. The method of claim 1, wherein the detectable label is selected from the group consisting of a radioactive label, a fluorescent label, a nuclear magnetic resonance active label, a luminescent label, a chromophore label, a positron emitting isotope for PET scanner, a chemiluminescence label and an enzymatic label.

* * * * *